(12) United States Patent
Krauss et al.

(10) Patent No.: US 8,467,859 B2
(45) Date of Patent: Jun. 18, 2013

(54) METHOD AND DEVICE FOR DERIVING AND EVALUATING CARDIOVASCULAR INFORMATION FROM CURVES OF THE CARDIAC CURRENT, IN PARTICULAR FOR APPLICATIONS IN TELEMEDICINE

(75) Inventors: Manfred Krauss, Chemnitz (DE); Joachim Schlund, Chemnitz (DE); Olaf Hartmann, Jena (DE); Jörg Schubert, Chemnitz (DE)

(73) Assignee: Telozo GmbH, Wien-Flughafen (AT)

( * ) Notice: Subject to any disclaimer, the term of this patent is extended or adjusted under 35 U.S.C. 154(b) by 681 days.

(21) Appl. No.: 12/310,649

(22) PCT Filed: Sep. 4, 2007

(86) PCT No.: PCT/EP2007/059248
§ 371 (c)(1),
(2), (4) Date: Jun. 7, 2010

(87) PCT Pub. No.: WO2008/028912
PCT Pub. Date: Mar. 13, 2008

(65) Prior Publication Data
US 2010/0331711 A1    Dec. 30, 2010

(30) Foreign Application Priority Data
Sep. 7, 2006  (AT) .................. A 1499/2006

(51) Int. Cl.
*A61B 5/0452* (2006.01)

(52) U.S. Cl.
USPC .......................... 600/509; 600/521

(58) Field of Classification Search
USPC ................................ 600/509, 521
See application file for complete search history.

(56) References Cited

U.S. PATENT DOCUMENTS

| | | | |
|---|---|---|---|
| 4,993,423 A | 2/1991 | Stice | 128/696 |
| 5,690,118 A | 11/1997 | Sornmo et al. | 128/696 |
| 5,713,365 A | 2/1998 | Castelli | 128/696 |

(Continued)

FOREIGN PATENT DOCUMENTS

| | | |
|---|---|---|
| DE | 19510382 | 9/1996 |
| DE | 19523199 | 1/1997 |

(Continued)

OTHER PUBLICATIONS

Schwab, et al., *Nichtinvasive Risikostratifikation bei koronarer Herzerkrankung: Stellenwert des Langzeit—EKG*; Deutsches Arzteblatt, vol. 44, Oct. 31, 2003, pp. A2878-A2882; XP002468386. (with English Abstract).

(Continued)

*Primary Examiner* — Christopher D Koharski
*Assistant Examiner* — Michael Carey
(74) *Attorney, Agent, or Firm* — Gerald T. Bodner

(57) ABSTRACT

The invention relates to a method and a device for deriving and evaluating cardiovascular information from curves of the cardiac current, in particular for applications in telemedicine. According to the invention, for data reduction purposes, a mean value and a standard deviation across the whole recording time are initially determined from a recorded ECG from the high-resolution signal, after which the RR intervals are assessed by means of an identification algorithm and only the results obtained are transmitted and/or recorded, for the purpose of data reduction.

3 Claims, 13 Drawing Sheets

U.S. PATENT DOCUMENTS

Figure 1:
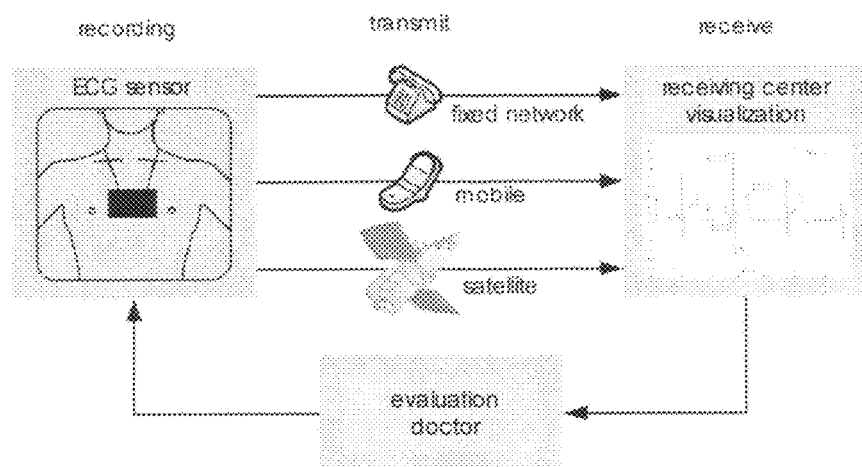

| | | | |
|---|---|---|---|
| 5,876,349 A | 3/1999 | Wang et al. | 600/518 |
| 5,967,994 A | 10/1999 | Wang | 600/509 |
| 6,282,440 B1 | 8/2001 | Brodnick et al. | 600/512 |
| 6,421,554 B1 | 7/2002 | Lee et al. | 600/509 |
| 6,496,722 B1 | 12/2002 | Schmidt | 600/513 |
| 6,685,649 B2* | 2/2004 | Korhonen | 600/485 |
| 7,236,818 B2 | 6/2007 | McLeod et al. | 600/509 |
| 2004/0193064 A1 | 9/2004 | Shusterman | 600/504 |
| 2004/0267142 A1* | 12/2004 | Paul | 600/509 |
| 2006/0020218 A1 | 1/2006 | Freeman et al. | 600/509 |
| 2006/0122470 A1 | 6/2006 | Schulz | 600/300 |
| 2006/0287605 A1* | 12/2006 | Lin et al. | 600/521 |
| 2010/0049066 A1* | 2/2010 | Hatakeyama | 600/509 |

FOREIGN PATENT DOCUMENTS

| | | |
|---|---|---|
| DE | 19830316 | 2/1999 |
| DE | 19749768 | 5/1999 |
| DE | 19902253 | 10/1999 |
| DE | 19954856 | 7/2000 |
| DE | 20008602 | 8/2000 |
| DE | 10065578 | 8/2001 |
| DE | 29924092 | 2/2002 |
| DE | 20118850 | 5/2002 |
| DE | 69617564 | 8/2002 |
| DE | 10247435 | 6/2003 |
| DE | 10245143 | 8/2003 |
| DE | 20306009 | 8/2003 |
| DE | 20309617 | 8/2003 |
| DE | 10233071 | 2/2004 |
| DE | 102006002045 | 8/2006 |
| EP | 0256886 | 2/1988 |
| EP | 0657136 | 6/1995 |
| EP | 0739181 | 10/1996 |
| EP | 0746229 | 12/1996 |
| EP | 0760225 | 3/1997 |
| EP | 0800787 | 10/1997 |
| EP | 0855167 | 7/1998 |
| EP | 0864294 | 9/1998 |
| EP | 0906058 | 4/1999 |
| EP | 1110502 | 6/2001 |
| EP | 1157659 | 11/2001 |
| EP | 1459681 | 9/2004 |
| EP | 1459681 A1 * | 9/2004 |
| EP | 1611843 | 1/2006 |
| WO | WO 96/19939 | 7/1996 |
| WO | WO 96/27326 | 9/1996 |
| WO | WO 98/09226 | 3/1998 |
| WO | WO 98/40011 | 9/1998 |
| WO | WO 99/04687 | 2/1999 |
| WO | WO 99/08592 | 2/1999 |
| WO | WO/99/23944 | 5/1999 |
| WO | WO 99/44500 | 9/1999 |
| WO | WO 99/56619 | 11/1999 |
| WO | WO 00/74564 | 12/2000 |
| WO | WO 00/76395 | 12/2000 |
| WO | WO 01/13791 | 3/2001 |
| WO | WO 02/24068 | 3/2002 |

OTHER PUBLICATIONS

American Heart Association, Inc., "*Heart rate variability. Standards of measurement, physiological interpretation, and clinical use. Task Force of the European Society of Cardiology and the North American Society of Pacing and Electrophysiology*"; European Heart Journal, The European Society of Cardiology, vol. 17, No. 3, Mar. 1996, pp. 354-381; XP002342325.

Notification of Transmittal of Translation of the International Preliminary Report on Patentability, English translation of the International Preliminary Report on Patentability and English translation of the Written Opinion of the International Searching Authority.

Bürklein M., et al., *Messverfahren zur Erfassung der Herzfrequenzvariabilität—Eine vergleichende Studie (Cross validation of heart rate variability measurements before and after exercise)*; Deutsche Zeitschrift Für Sportmedizine, Jahrgang 56, Nr. 12, 2005 (pp. 415-421).

Baumert, J.H. et al., "*Analyse der Herzfrequenzvariabilität: Grundlagen, Methodik und mögliche Anwendurgen in der Anästhesie (Analysis of heart rate variability. Background, methods, and possible use in anaesthesia)*", Anaesthesist 44 (10), Oct. 1995, pp. 677-686.

Horn, Andrea, "*Diagnostik der Herzfrequenzvariabilität in der Sportmedizin—Rahmenbedingungen und methodische Grundlagen (Diagnostics of the heart rate variability in sports medicine—frame conditions and methodical bases)*", dissertation at Ruhr-Universität Bochum, Dec. 2003.

Schwab, et al., "*Non-invasive Risikostratifikation with coronary artery disease: role of Holter ECG*", Deutsches Arzteblatt, vol. 44, Oct. 31, 2003, pp. A2878-A2882; XP002468386 (in English).

\* cited by examiner

Figure 12:
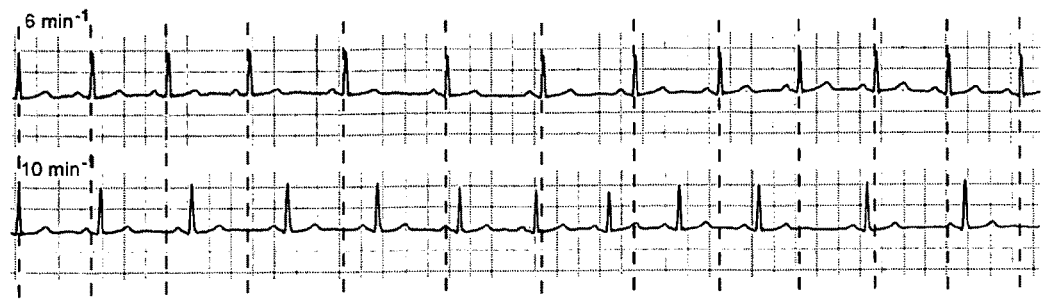

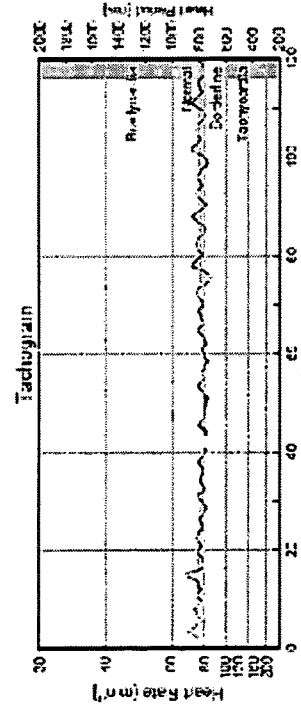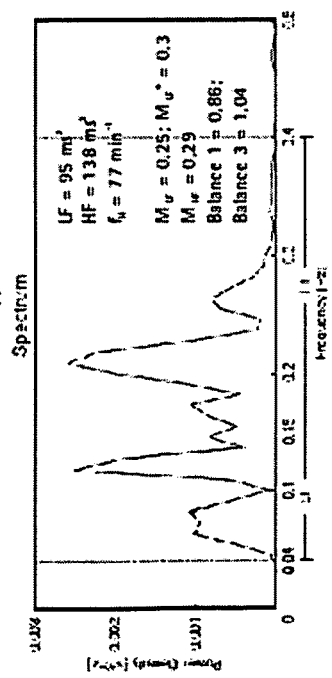
Figure 12 a), b)

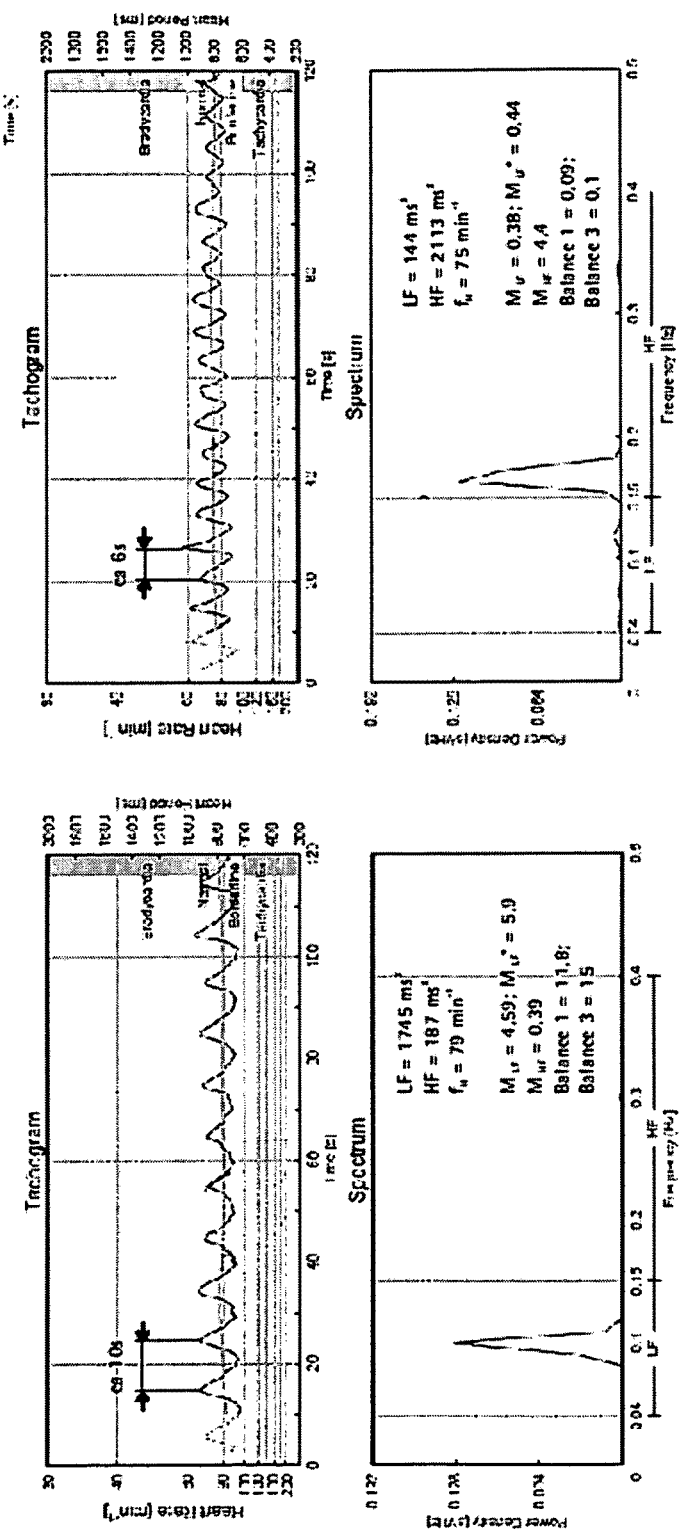
Figure 12 c), d)

METHOD AND DEVICE FOR DERIVING AND EVALUATING CARDIOVASCULAR INFORMATION FROM CURVES OF THE CARDIAC CURRENT, IN PARTICULAR FOR APPLICATIONS IN TELEMEDICINE

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC

Not Applicable

BACKGROUND OF THE INVENTION (1) Field of the Invention

The invention relates to a method and a device for deriving and evaluating cardiovascular information from electrocardiograms, especially for telemedical applications.

(2) Description of Related Art

As a consequence of the progression of cardiovascular diseases and the limited therapeutic possibilities in the late stages, there is the necessity of an early and complex cardiovascular diagnosis, during which above all also the interaction of the heart with the rest of the peripheral circulation system has to be assessed at the same point of time and at any time of the day. Most of the hitherto known measuring methods show disadvantages as far as their evaluation is concerned, for both the patient and the responsible doctor who has to derive therefrom a diagnosis. Telemetrical requirements hardly get any attention.

Under the cardiovascular aspect, the electrocardiogram (ECG) based on the known limb and thorax leads represents the most widely spread diagnostics and monitoring method, though it brings along a number of inadequacies because the ECG detects electrical phenomena at the heart, while the entire cardiovascular system is not sufficiently represented. Therefore, there is the necessity to determine additional information contained in the ECG as comprehensively as possible. In consideration of a telemedical application, a device to be developed must take into account the following priorities:
 easy and reliable handling,
 not dangerous to the user
 cost-efficient
 easy and modular evaluation possibility for both the doctor and the user.

In general, telemedicine is a broadly defined comprehensive term which stands for the use of multimedia communication and information technologies in the health sector. In a narrower sense, it describes the actual application of different technologies to render individual services in the field of medical engineering, by simultaneously bridging the physical distance between the doctor and the patient.

Hence, it appears that telemedicine allows a reduction of the relative risk which is, in many cases, caused by claiming medical aid too late and, thus, of the deterioration of the prognosis. A substantial prerequisite for this are the practicability and reliability of the cardiovascular parameters, which the user himself derives and transmits telemetrically.

FIG. 1 shows the general functional diagram of a tele-ECG: recording, transmitting, receiving, analyzing. Significant is here the result of performed analyses: Patients, who were connected to the telemedical service, reacted fast and determined. Nearly 90% of them contact the telemedical center within one hour after the troubles began.

The use of telemedical technologies involves special requirements, which hardly arise with the known ECG recordings.

In the field of the mobile detection and storage of electrocardiogram signals specifically for the use in medicine and sports, the prior art is extensive. Examples are:

DE 197 49 768 A1 (Plaster with data recording function for the detection and storage of electrocardiogram signals), PCT/DE98/033225 (Evaluation of electrocardiograms in the field of extrasystoles), PCT/US99/09336 (Elektrocardiography Electrodes Holder), DE 198 30 316 A1 (Method and device for detecting ventricular fibrillation), WO 99/04687 (Remote Monitoring Apparatus for Medical Conditions), DE 199 02 253 A1 (Method and system for characterizing the quality of cardiac function indicating signals), PCT/US99/03666 (A System and Method for Detecting and Locating Heart Disease), PCT/US98/16693 (Automatic Cardiometer), EP 0 760 225 A1 (Method and apparatus for correcting for non-physiological variations in ECG signals), EP 0 800 787 A1 (Device for monitoring measurements electrodes, devised for picking up physiological measurement signals, and their leads), EP 0 855 167 A1 (Multiple ECG electrode strip), EP 0 864 294 A2 (Detecting abnormal activation of the heart), PCT/GB98/00742 (Method of Analyzing a cardiac signal), DE 195 23 199 A1 (Method for representing ECG signals), DE 195 10 382 A1 (Portable device for detecting ECG data), PCT/US96/02826 (Method and apparatus for detecting artifacts using common mode signals in differential signal detectors), PCT/BE95/00123 (A device and a method for recording and monitoring cardiac activity signals), EP 0 657 136 A1 (Electrocardiograph), DE 199 54 856 A1 (Method and device for detecting a connection error of a telemetrical biomedical device), DE 200 08 602 U1 (Volks-ECG), PCT/AU00/00656 (Cycling event and auto-trigger memory handling), PCT/US99/18296 (Ambulatory physio-kinetic monitor), DE/EP 0 746 229 T1 (Measurement and evaluation of the electrical stability of the heart), PCT/IL00/00506 (Compact electrode assembly for a portable ECG signaling device), EP 1 110 502 A2 (Clinical research workstation), DE 100 65 578 A1 (Method for identifying an electrode placement), DE 102 47 435 A1 (Interpretation manual electrocardiograph), EP 1 157 659 A1 (Method and apparatus for reducing noise and detecting electrode faults in medical equipment), DE 102 45 143 A1 (Method for evaluating electrocardiograms), DE 102 33 071 A1 (Method and system for the measurement, the analysis and the wireless transmission of cardiac potentials), WO 02/24068 A1 (Method and system for detection of cardiac arrhythmia), A 61 B 5/0404 (Portable ECG recorder, Utility Model Document), DE 201 18 850 U1 (Portable measuring device for ECG analysis), DE 203 09 617 U1 (Simulation device to output test signals to electrocardiographs, Utility Model Document), DE 203 06 009 U1 (System for the measurement, the analysis and the wireless transmission of cardiac potentials, Utility Model Document), DE 299 24 092 U1 (ECG recorder, Utility Model Document), EP 0 739 181 B1 (Sudden cardiac death prediction), EP 0 906 058 B1 (Device for the frequency analysis of atrial fibrillation), DE 696 17 564 T2 (Pocket device for the detection of an electric biological signal, especially an electrocardiographic signal).

As is generally known, an electrocardiogram (ECG) represents, in its most general form, the variation of bioelectrical signals or potential differences, respectively, over time, which occur during the depolarization and repolarization in the heart. From this, among others direct indications to arrhythmias or indirect indications to acute myocardial infarctions or post-infarctions can be derived.

Beside the dependency of the (mean) heart rate on the age, it is known from physiology that the activity of the autonomic nervous system significantly influences the heartbeat duration and the entire cardiovascular condition. While a sympathetic stimulation reduces the heartbeat duration by a release of adrenalin and noradrenalin, that is, it increases the rate, it is known that the parasympathetic nervous system causes a heart rate reduction largely by the release of acetylcholine. The latter relates above all to the state when the body is at rest in a horizontal position (vagal stimulation).

OBJECTS AND SUMMARY OF THE INVENTION

As the electrocardiogram can be determined for each cardiac beat within one lead while, on the other hand, an electrocardiogram implies the registration of the excitation behaviors of the atriums and ventricles, and this time function requires low-frequency limits of about 0.05 Hz for detecting the activity of the autonomic nervous system, it is the object to determine the cardiovascular information necessary for the cardiovascular behavior from the total ECG time function derived, including superimpositions.

A method for deriving and evaluating cardiovascular information from electrocardiograms, especially for telemedical applications, in accordance with one form of the present invention, results in the reduction of data. A mean value and a standard deviation are initially determined from the high-resolution signal of a recorded ECG over the total recording time and the R-R intervals are subsequently evaluated by means of a detection algorithm, and only the received results are transmitted and/or recorded for the data reduction.

These and other objects, features and advantages of the present invention will be apparent form the following detailed description of illustrative embodiment therefore, which is to be read in connection with the accompanying drawings.

BREIF DESCRIPTION OF THE DRAWINGS

The invention shall be explained in more detail below on the basis of the following description and by means of embodiments and figures. The figures show:

FIG. 1: a functional diagram of a tele-ECG.

Figure 2:
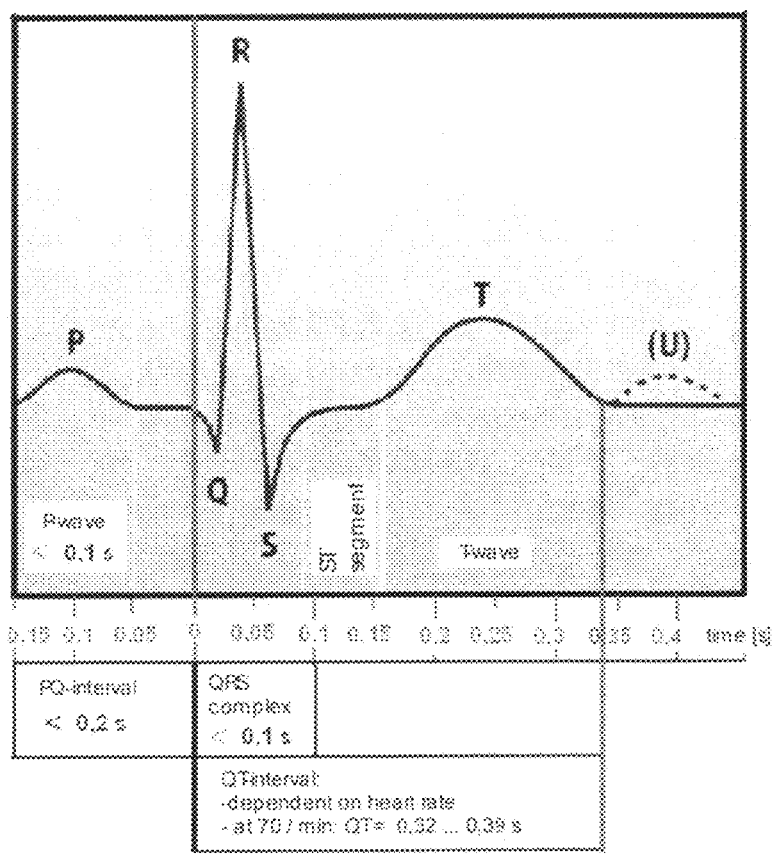

FIG. 2: signal-averaged ECG form of all normal ("periodical") ECG intervals superimposed during the ECG recording time by the example of a 20 year old subject in a healthy cardiovascular condition.

Figure 3:
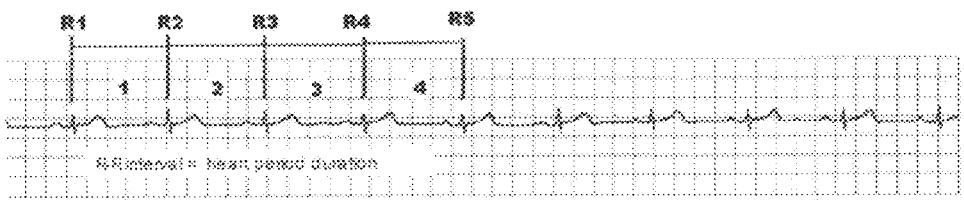

FIG. 3: a time section of a 1-channel tele-ECG, including marked R-R intervals as pertinent heart period durations.

Figure 4:
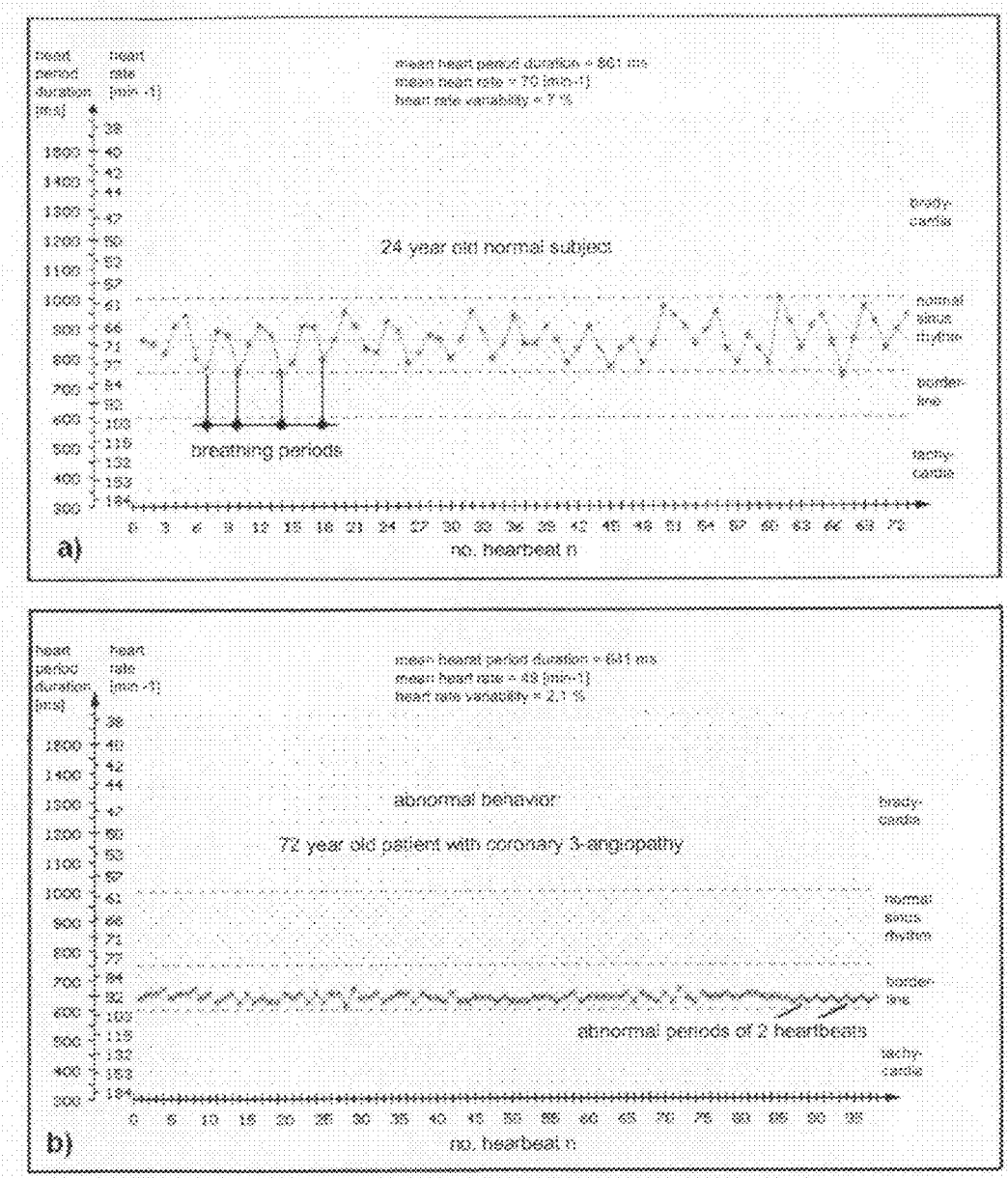

FIG. 4: a time section of 1 minute of a tachogram of the heart period durations (R-R intervals) and the reciprocal value heart rate thereof:
a) 24 year old normal subject: it clearly shows a respiratory sinus arrhythmia with the respiratory periods. Also, a distinct heart rate variability can be seen.
b) 72 year old patient having a coronary 3-angiopathy: beside the high mean heart rate of 94 min$^{-1}$ the heart rate variability is obviously low. A respiratory sinus arrhythmia is not developed. At the end of the 60s-tachogram the heart period durations change periodically with the abnormal period of 2 heartbeats, with the change amplitudes being low.

Figure 5:
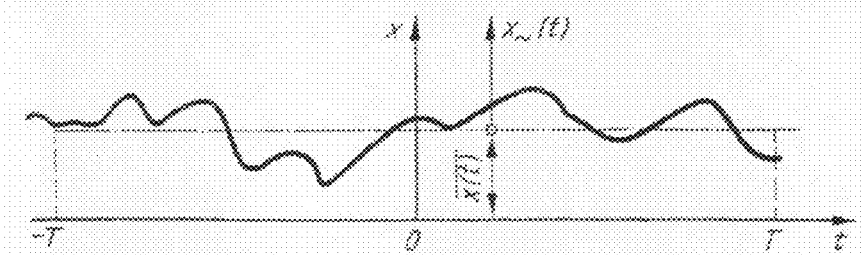

FIG. 5: signal x(t), pertinent linear mean value $\overline{x(t)}$ and alternating component x_(t).

Figure 6:
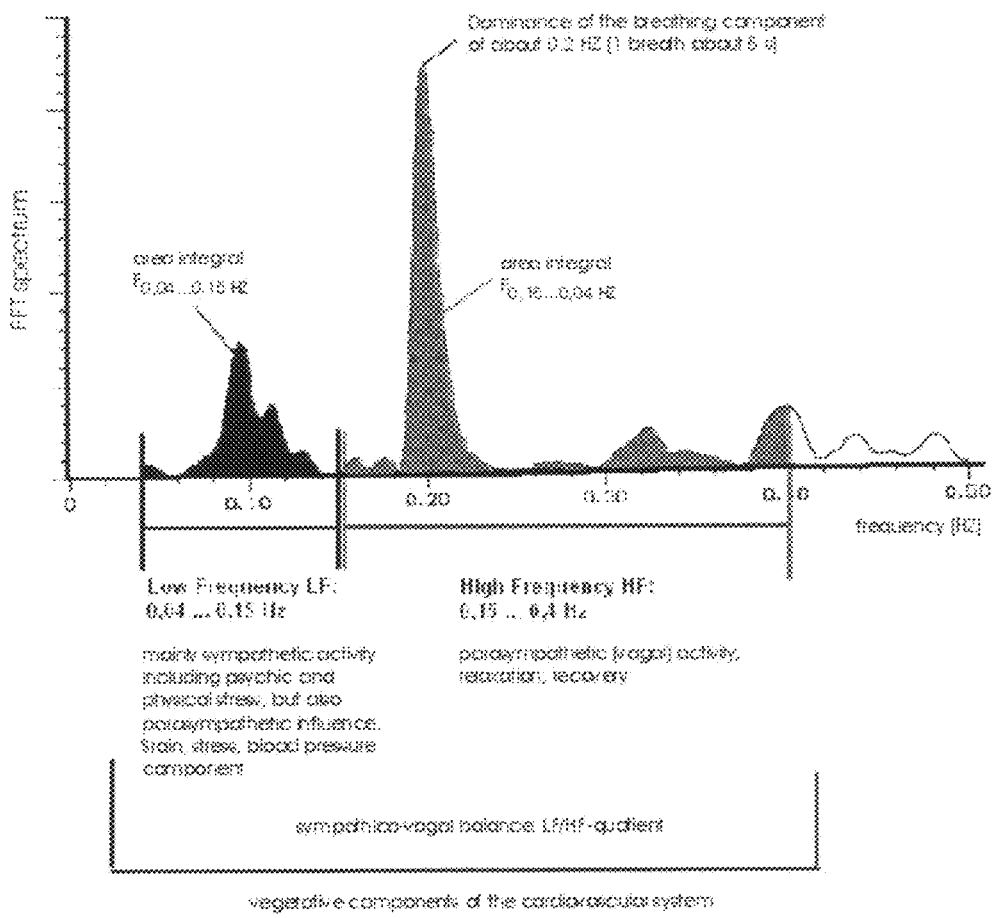

FIG. 6: FFT-spectrum derived from the tachogram of the heart period durations of a 20 year old healthy subject with a 3 minute derivation time [according to Baumert, J-H, A W Frey and M Adt: Analysis of the heart rate variability. Basics, methodology and possible use in anaesthesia. Anaestesist 44 (1995), 677-686] including frequency range characteristics [according to: Heart rate variability. Standards of measurement, physiological interpretation and clinical use. European Heart Journal (1996) 17, 354-381].

Figure 7:
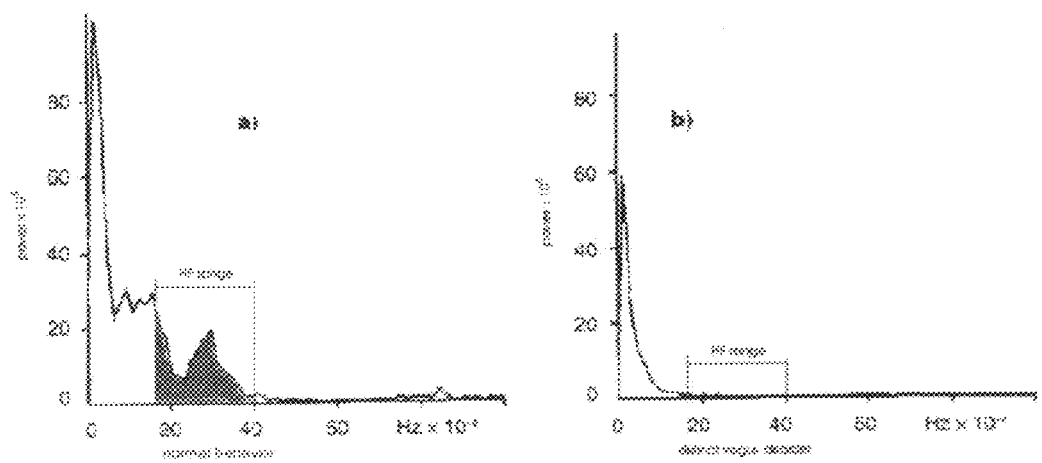

FIG. 7: spectral power density of the heart rate variation of resting, lying persons and an ECG measurement time of 5 minutes:
a) a 35 year old normal subject: the frequency components are in all 3 ranges within the (herein not specified) standard limits
b) 35 year old type I diabetic with somatovisceral polyneuropathy of a moderate degree: the differences in the LF and HF range are considerable, above all in the HF range.

Figure 8:
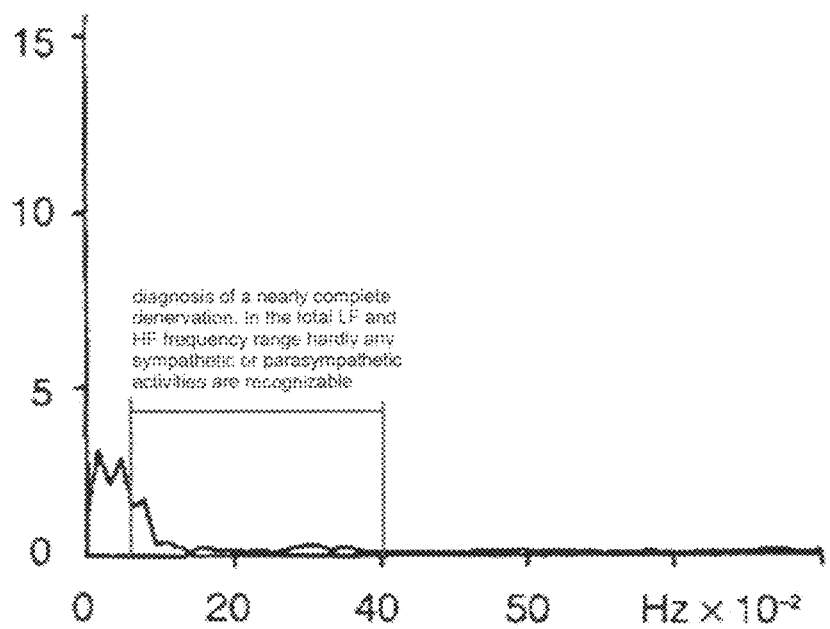

FIG. 8: spectral power density of the heart rate variation of a resting, lying 37 year old patient having Guillain-Barré-Strohl polyradiculitis. There is an extreme power reduction in both frequency ranges (note: more sensitive scale used than in FIG. 7).

Figure 9:
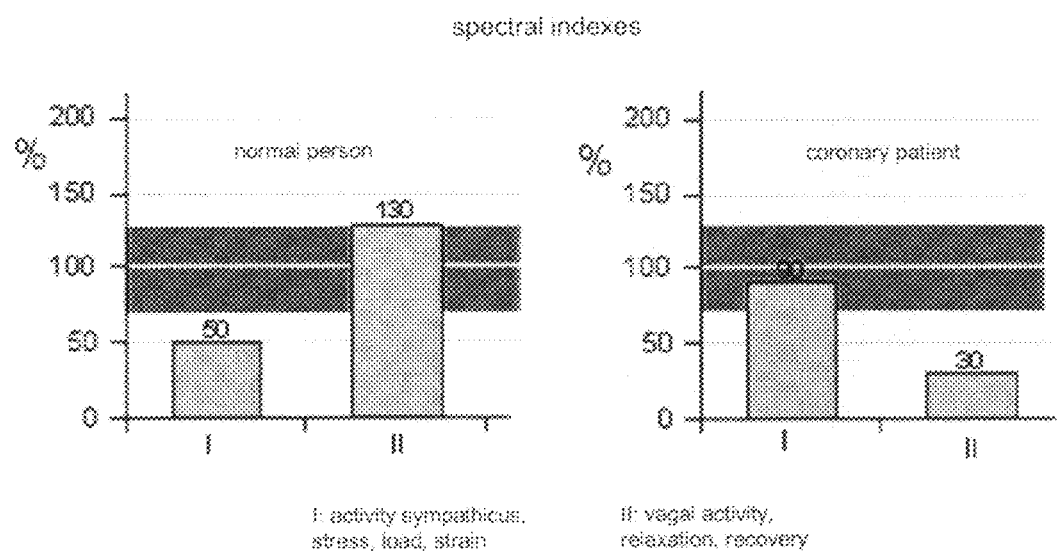

FIG. 9: characteristic examples of spectral indexes:
left: for a normal subject corresponding to FIG. 4a), right: for a coronary patient according to FIG. 4b).

Figure 10:
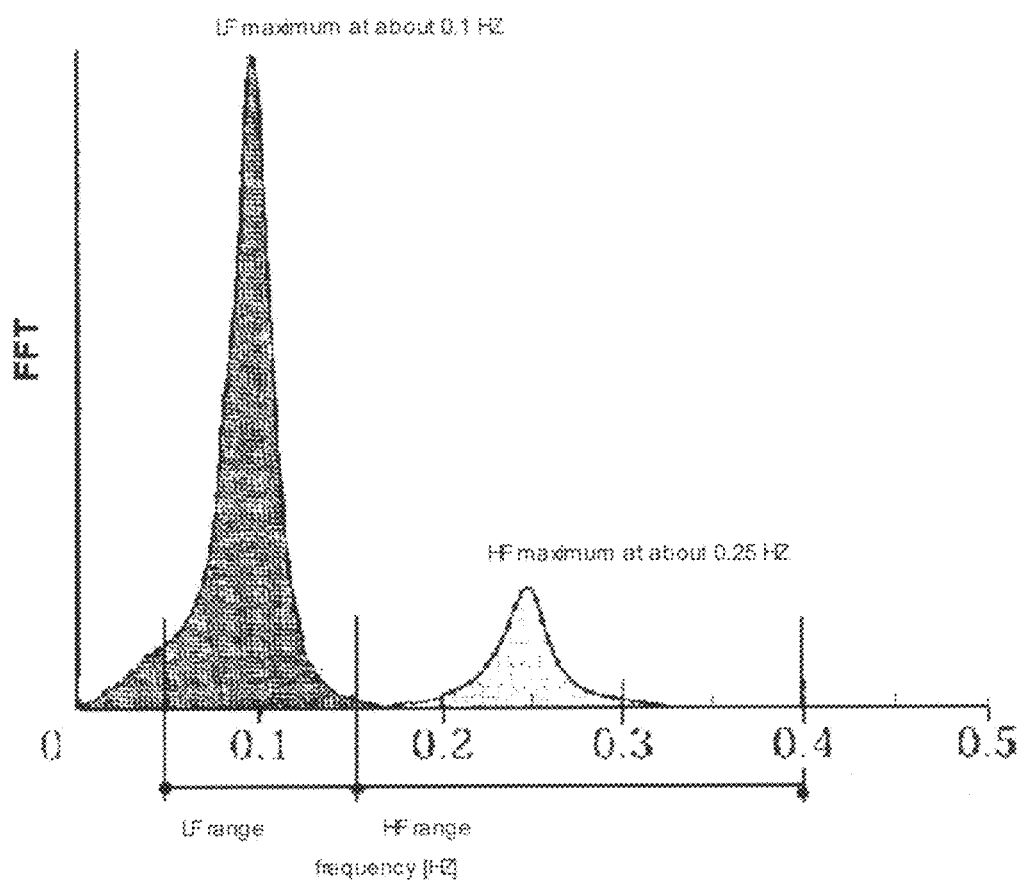

FIG. 10: smoothing of an FFT spectrum derived from the heart period duration tachogram of a 28 year old lying normal person.

Figure 11:
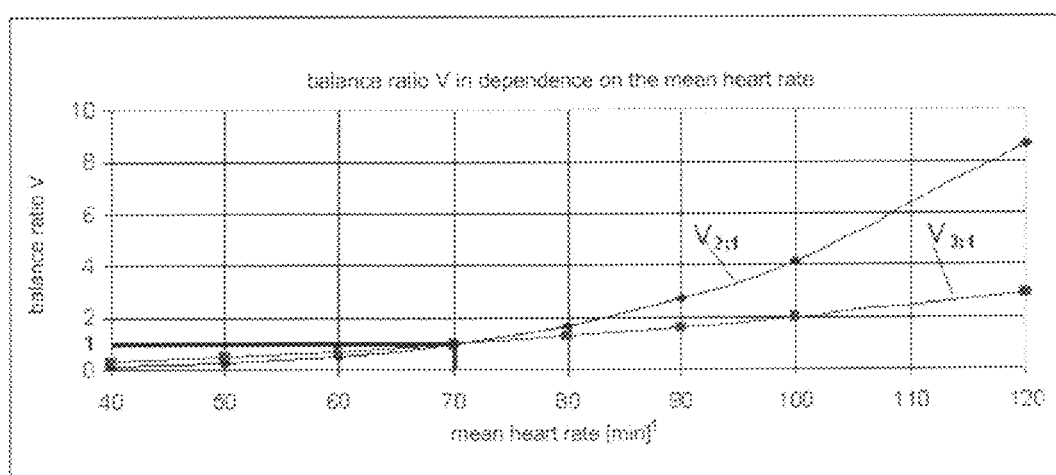

FIG. 11: dependence of the defined balance ratio $V_{balances}$ of the mean heart rate $f_H$. It can be seen that both weightings do not differ at a normal heart rate of 70 min$^{-1}$, while lower and higher heart rates lead to obvious differences.

FIGS. 12a), b): heart period duration tachograms and pertinent FFT spectrums as well as cardiovascular parameters, derived from a tele-ECG of a 30 year old lying test subject (smoker) at rest and subjected to a reflex vasoconstriction (passive sudden immersion of the left hand in ice water). It is pointed out that the power spectrums under a) and b) show different scales [the sensitivity in Fig. a) is four times higher].

FIGS. 12c), d): heart period duration tachograms and pertinent FFT spectrums as well as cardiovascular parameters, derived from a tele-ECG of a 30 year old lying test subject (smoker) according to FIG. 12a) with more intensive breast breathing of 6 to 10 min$^{-1}$.

FIG. 12e): time section of the tele-ECG of the lying test person according to FIGS. 12 c) and d) with more intensive breast breathings of 6 to 10 min$^{-1}$. Obvious differences in the R-R intervals can be seen both during inspiration and expiration as well as in the cardiovascular parameters as a whole [see FIGS. 12 c) and d)].

Figure 13:
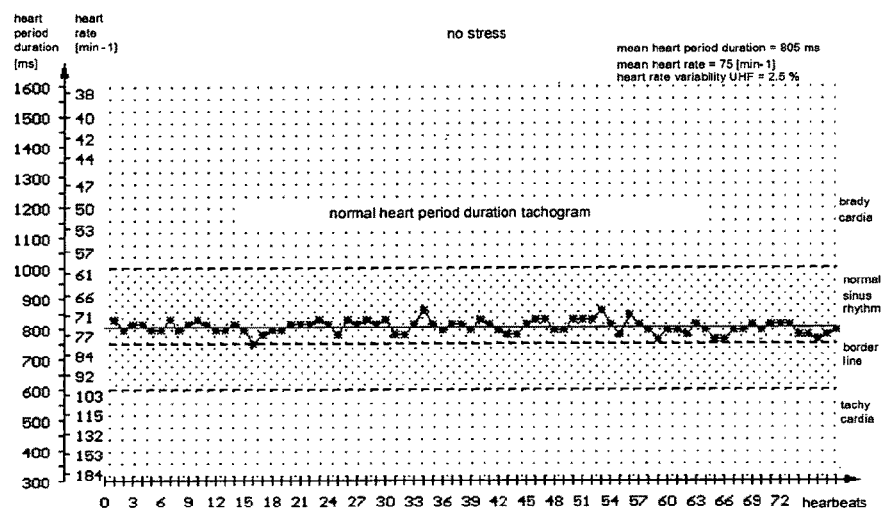
Figure 13:
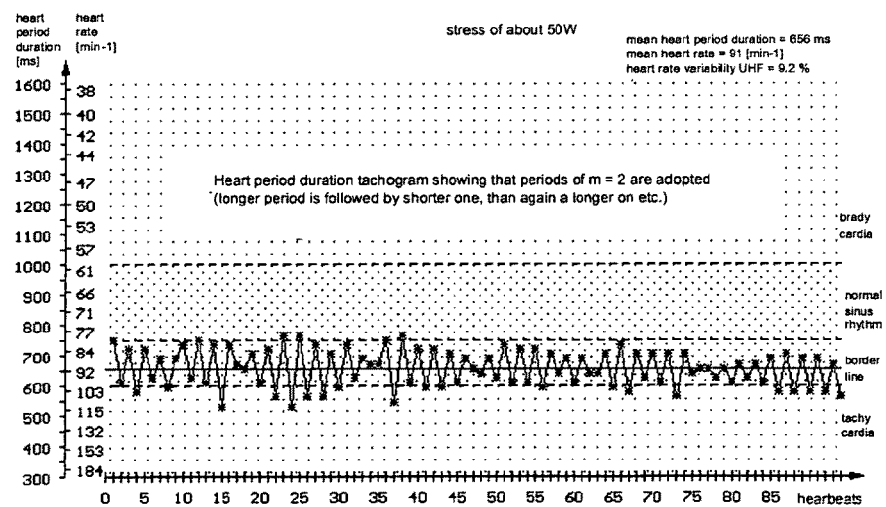

FIG. 13: behavior of the heart period duration tachograms of a 68 year old heart rehabilitation patient before and during ergonometer exercise. At a stress of 50 W the heart period durations change, partially like an electronic multivibrator.

Figure 14:
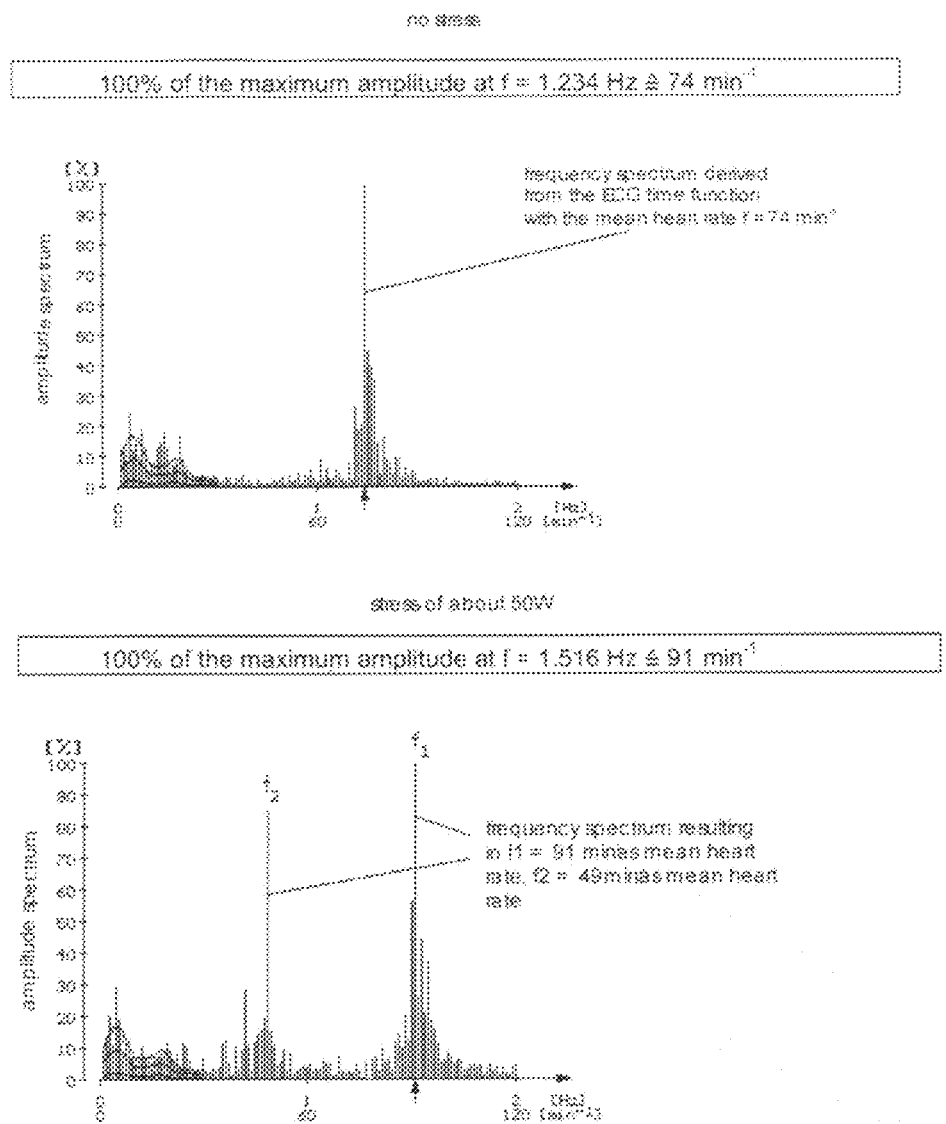

FIG. 14: amplitude spectrums, derived from the pertinent ECG time functions for the test person and the conditions according to FIG. 13.

Figure 15:
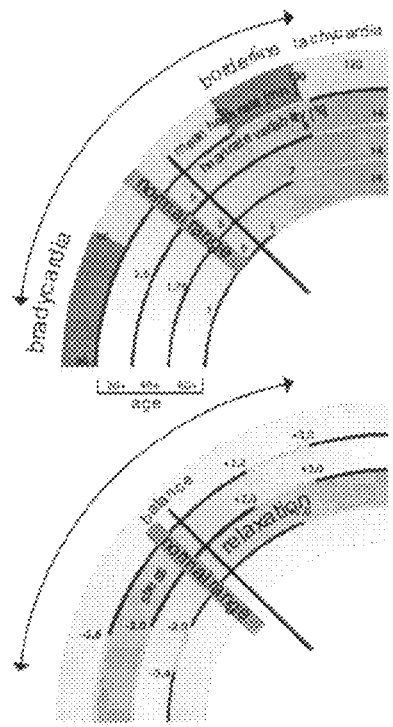

FIG. 15: tachometer-like surface design on a display of a mobile radio device or terminal, respectively, by means of a telemedical data transfer of cardiovascular parameters. In a modification, the pointer is stationary, while the scale parts are varied in accordance with their values.

Figure 16:
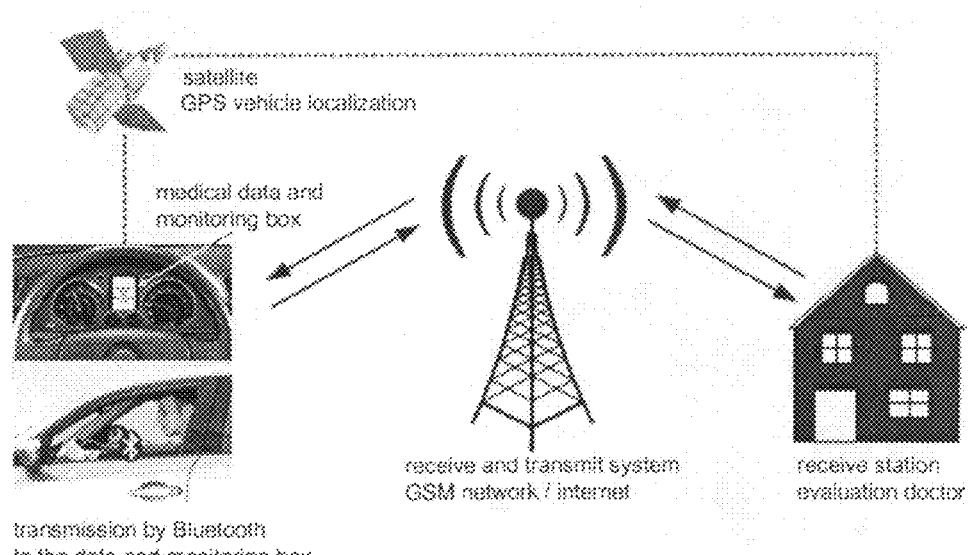

FIG. 16: recording and detection of vital data in the passenger car or truck, especially ECG, blood pressure and blood oxygen saturation to a medical data and monitoring box, and subsequent telemedical transmission and evaluation in a receive station. A permanent vehicle localization, and in an emergency even communication, is possible via satellite.

Figure 17:
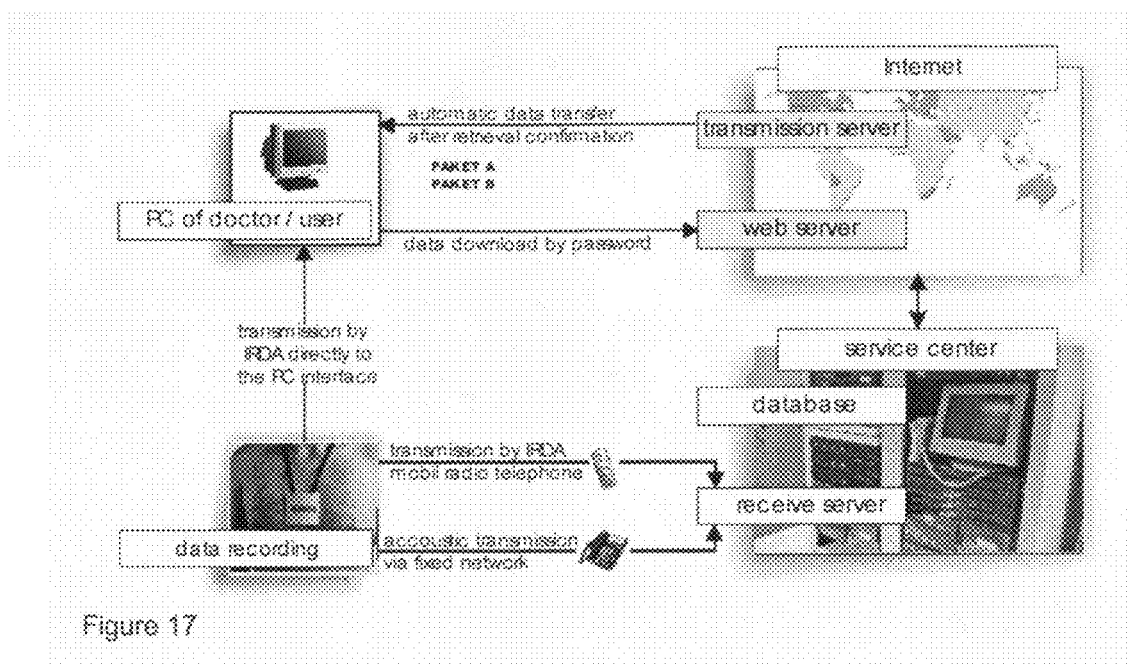

FIG. 17: communication process of the ECG recording and storage and the telemedical data transfer by using the most various analog and digital communication paths.

Figure 18:
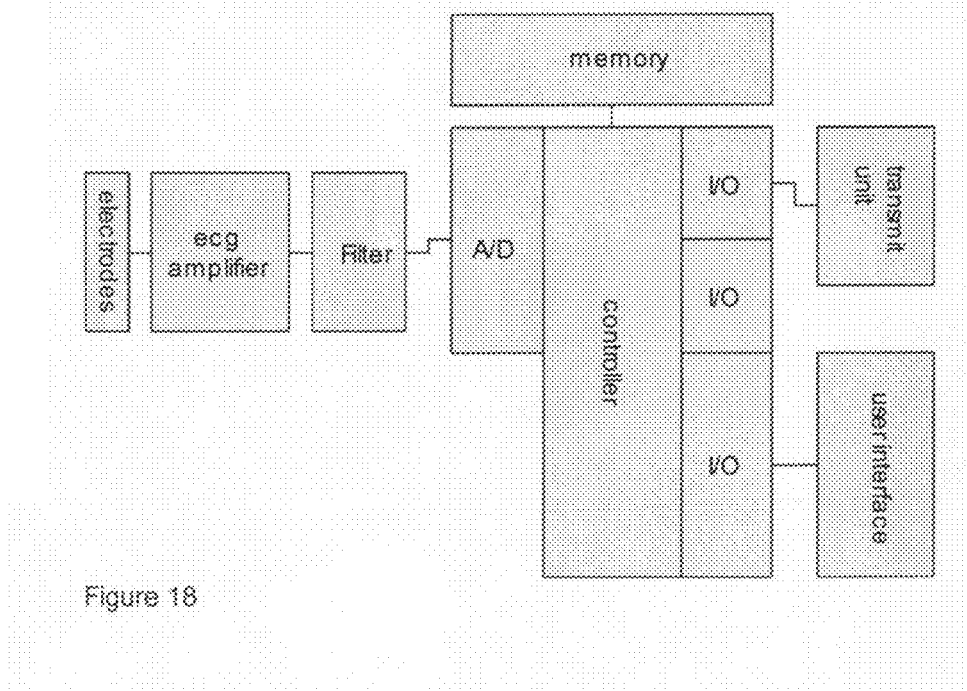

FIG. 18: general schematic representation of a telemedical ECG sensor, including signal processing and storage as well as user interface and transmit unit.

Figure 19:
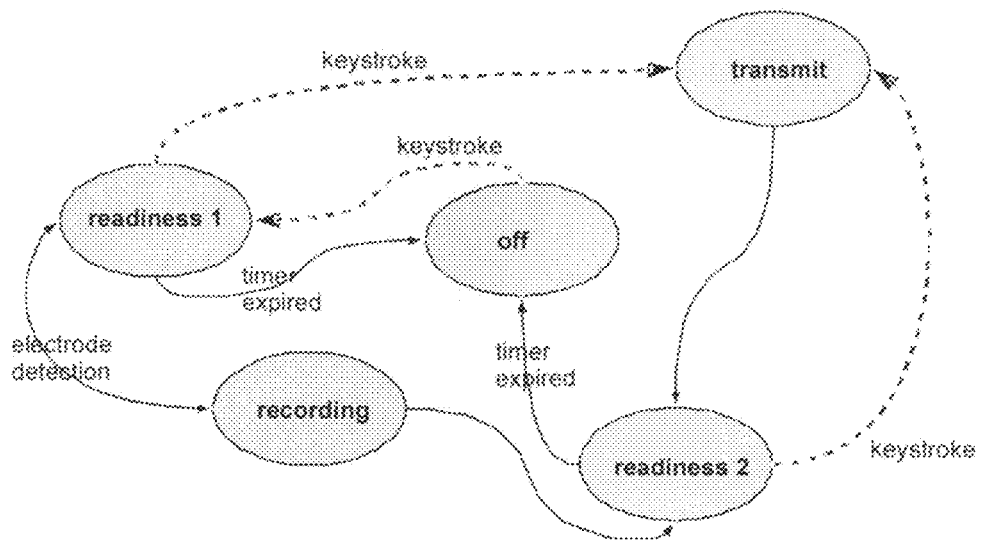

FIG. 19: automat graph 1-key operation.

Figure 20:
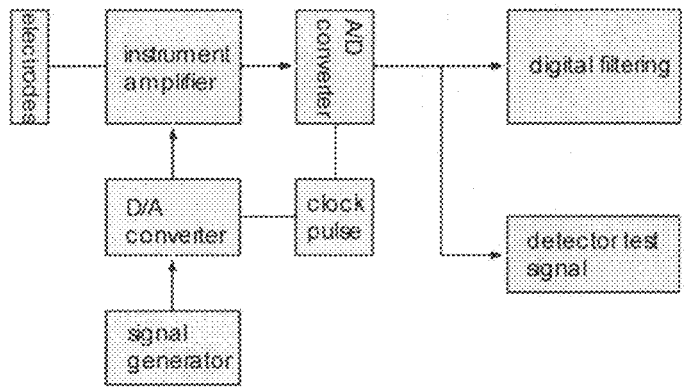

FIG. 20: block diagram for the detection of amplitudes.

Figure 21:
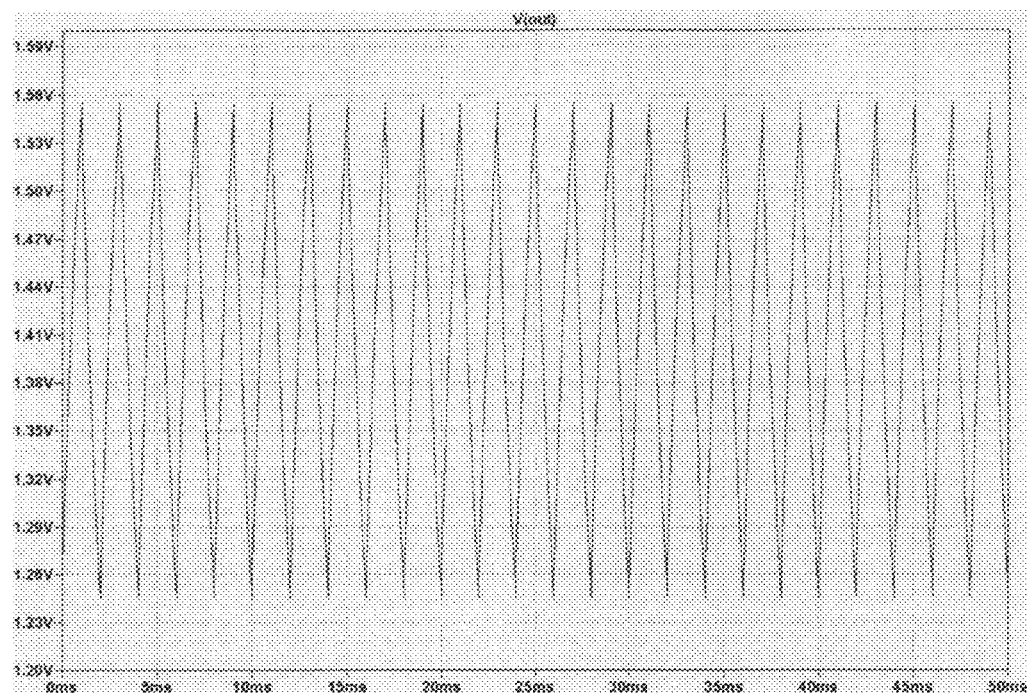

FIG. 21: test signal (0.0013671875 mVss/500 Hz) in the case of open electrodes.

Figure 22:
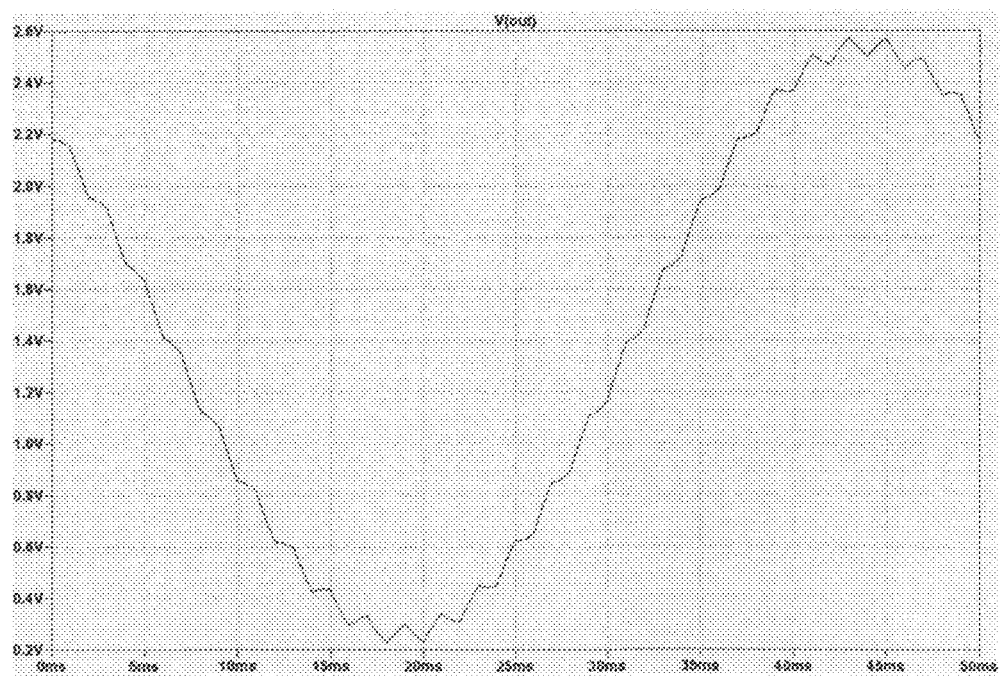

FIG. 22: attenuated test signal with superimposed 20 Hz wanted signal 6 mVss in the case of connected electrodes.

DETAILED DESCRIPTION OF THE PREFERRED EMBODIMENTS

As is well known from the analysis of signals, recorded data can be analyzed in the
- time domain
- frequency domain
- amplitude range While in the time domain the behavior of the measured quantity is represented as a function of time, the frequencies in the signal obtained by the known discrete Fourier transform are of equal interest as the data analysis in the amplitude range. Typical questions in connection with the latter are, for example, the distribution of the data, mean values and spread.

In this complex sense, according to the invention, the ECG signals derived are analyzed in order to achieve the object to determine specific cardiovascular information from the ECG time function under the aspect of a telemetric transmission. To this end, a time-discrete telemetric ECG analysis is performed.

In the center of the method and the device for deriving cardiovascular information from electrocardiograms for telemedical applications are dynamic processes, characterized specifically by the detection and evaluation of heart period durations (R-R intervals in the ECG) within a measurement or derivation time adapted to the telemetric transmission.

Thus, it is known that, during the evaluation of the durations of the heartbeats, the so-called R-R intervals of an ECG, the informative content is substantially increased as compared to that in a form analysis of ECG intervals. This likewise relates to the telemedically transmitted electrocardiogram which, in most cases, was so far evaluated merely qualitatively, above all also in view of occurring arrhythmias.

In a first step, the actual ECG interval, the form thereof, is analyzed from a recorded ECG. To this end, all "normal ECG intervals" (i.e. without extrasystoles etc.) detected during an ECG recording time of, for example, 2 minutes are superimposed, and the mean interval, the form thereof, is determined and graphically represented as "signal-averaged ECG form" to allow a comparison with a normal behavior. Here, only time values from the recorded tele-ECG are analyzed, that is, no amplitude evaluations are made. This permits an easy and immediate comparison of the set behavior with the actual behavior, which can be seen in FIG. 2 by the example of a 20 year old test person in a healthy cardiovascular condition. Also, the representation of the late potentials occurring in the time average is possible, wherein late potentials are, as is well known, high-frequency, low-amplitude signals at the end of a QRS complex, which have their origin in regions of a damaged ventricular myocardium with a slowed down conduction. As the amplitude thereof in the surface ECG is very low, late potentials can only be derived upon a high amplification and by means of specific methods for the suppression of noise, which is possible according to the invention.

In a second step of the method, the R-R intervals are determined from the recorded ECG according to a corresponding detection algorithm (FIG. 3), all of which (that is, including extra beats) are graphically represented as heart period duration tachogram. Thus, for example, the occurrence of an absolute arrhythmia and of general arrhythmias can be visually seen at once.

To quantitatively determine the time and frequency parameters to be derived from the R-R tachogram, initially a proof test with respect to M analyzable ("normal") R-R intervals of the relevant measurement time is performed, whereby it is proceeded from the common definition that premature extra beats (25% prematureness relative to the mean R-R interval) and the post-extrasystolic beat are to be eliminated for the subsequent parameter determinations in the time and frequency domain, and that the heart-period-mean-value initially determined from all measurements is to be introduced at the same points of time.

After such a procedure, the mean heart periodicity is calculated anew ("to obtain a more precise value") from the detected M R-R intervals as known arithmetic mean value of the heart period durations $\overline{T_H}$ in [ms] as follows:

$$\overline{T_H} = \frac{1}{M}\sum_{\mu=1}^{M} T_\mu \quad [ms]$$

from which the mean heart rate $\overline{f_H}$ can be derived, based on the conversion:

heart rate $f_H$ [Hz]=1/heart period duration $T_H$ [s]

and heart rate $f_H$ [min$^{-1}$]=60/heart period duration $T_H$ [s].

In the tachogram of the heart period durations the following known cardiologic classification of the heart rate is to be made:

normal sinus rhythm: 60 . . . 80 min$^{-1}$ [heart period duration=750 . . . 1000 ms]

bradycardia: $\leqq$60 min$^{-1}$ [heart period duration$\geqq$1000 ms]

borderline: 80 . . . 100 min$^{-1}$ [heart period duration 600 . . . 750 ms]

tachycardia: $\geqq$100 min$^{-1}$ [heart period duration$\leqq$600 ms].

An absolute deviation of the heart period duration $\Delta T_H$ at the time of the μth heartbeat from the determined arithmetic mean value $\overline{T_H}$ applies according to FIG. 4

$$\Delta T_H(\mu) = T_H(\mu) - \overline{T_H}.$$

From this follows the "standard deviation" $s_{TH}$ or the clinically frequently used "absolute heart rate variability", respectively:

$$s_{TH}[\text{ms}] = \sqrt{\frac{1}{M-1}\sum_{\mu=1}^{M}[T_H(\mu) - \overline{T_H}]^2}$$

In order to minimize, for example, the influence of the known day/night rhythmicity, relative values are introduced, i.e. the absolute variability of the heart period duration $s_{TH}$ with the dimension "second", the standard deviation, is related to the mean heart period duration of the same dimension and, for the purpose of indicating percentage values, is multiplied by the factor 100. This cardiovascular parameter represents a "variation coefficient" and is abbreviated to "(relative) heart rate variability" VHF (ΔHF) and HRV, respectively.

$$HRV[\%] = \frac{s_{TH}[\text{ms}]}{\overline{T_H}[\text{ms}]} 100[\%]$$

Thus, this variation coefficient, the (relative) heart rate variability, is a mean value (for the purpose of the signal theory, an "effective value") and—also like the above-introduced mean heart periodicity—dependent on the age: the heart rate variability is reduced with an increasing age.

In the present case, the telemetric application is oriented by the absolute and relative standard deviations $S_{TH}$ and HRV=VHF, respectively.

As is well known, the changes of the heart period duration adopted per heartbeat under certain physiological conditions are an indication of the activity of the autonomic nervous system comprised of its components and, at the same time, so-called "adversaries" sympathetic and parasympathetic nervous systems. According to the invention the object to be achieved below is, therefore, to derive from a heart period duration tachogram the respectively associated information and quantitative indexes, including those for "stress". Thereby, it is physiologically known that there is a direct connection between physical stress reactions and the autonomic nervous system.

Stress is a medical and psychological phenomenon, which appears in all age groups and all social stratums. Many people try to compensate the everyday stress. As is well known, a very simple and effective means to reduce stress is physical exercise. Stress accumulated in the body is abreacted and processed during physical exertion, without causing damage to health. Regular reasonable exercise keeps the body fit, produces new self-confidence and increases the defense against stress impulses. The cardiovascular system gets stronger.

Moreover, it is known from physiology that the activity of the autonomic nervous system significantly influences the heart rate. While a sympathetic stimulation reduces the heartbeat duration by releasing adrenalin and noradrenalin, i.e. increases the rate, the parasympathetic nervous system causes a heart rate reduction mainly by the release of acetylcholine. The latter relates above all to the state while the body is at rest in a lying position (vagal stimulation).

This influence of the autonomic nervous system by the adopted mean heart rate on the evaluation of the cardiovascular state is frequently associated with the aforementioned "heart rate variability" too one-sidedly. This is deemed to be a decisive deficiency, especially also in the evaluation of "stress" and "strain" or the adversary "recovery". By means of the general signal theory it will be shown, in accordance with the invention, that an extended integral quantitative dimension can be derived therefor.

From the signal theory it is known that an optional time function x(t) can be generally decomposed into the arithmetic mean value $\overline{x(t)}$ and into an alternating component $x_\sim(t)$ (FIG. 5):

$$x(t) = \overline{x(t)} + x_\sim(t)$$

For the linear (arithmetic) mean value of x(t) one obtains $$\overline{x(t)} = \frac{1}{2T}\int_{-T}^{+T} x(t)dt.$$

As is generally known, $\overline{x(t)}$ directly corresponds to half the value of the Fourier coefficient $A_0$. For periodic signals, the period duration T is to be inserted for the determination of $\overline{x(t)}$, for non-periodic signals $$\overline{x(t)} = \lim_{T \to \infty} \frac{1}{2T}\int_{-T}^{T} x(t)dt.$$

applies. It follows for the root mean square value $$\overline{x^2(t)} = \frac{1}{2T}\int_{-T}^{T} x^2(t)dt,$$

analogously for non-periodic signals $$\overline{x^2(t)} = \lim_{T \to \infty} \frac{1}{2T}\int_{-T}^{T} x^2(t)dt.$$

Between the signal powers of the components x(t), $\overline{x(t)}$ and $x_\sim(t)$ the following basic relationship applies, which is known as parallel-axes theorem in mechanics:

$$\overline{x^2(t)} = [\overline{x(t)}]^2 + \overline{x_\sim^2(t)}$$

The total power of a signal is, accordingly, composed of the square of the linear (arithmetic) mean value as well as of the mean power of the alternating component, which corresponds to the square of the effective value $x_{eff}$:

$$x_{eff} = \sqrt{\overline{x^2(t)}}$$

According to the invention, this parallel-axes theorem can be applied to the "heart period duration tachogram function R-R interval". However, as with respect to the time t a measured value is obtained only after each heartbeat μ, instead of x(t) the above-introduced term $T_H(\mu)$ shall be used as basis for the following considerations. As was already substantiated, this total signal $T_H(\mu)$ is composed of the addition of the arithmetic mean value $\overline{T_H}$ and the absolute deviation of the heart period duration $\Delta T_H$ at the time of the µ-th heartbeat from the mean value:

$$T_H(\mu) = \overline{T_H} + \Delta T_H(\mu)$$

Analogously to the aforementioned parallel-axes theorem used in signal theory, consequently, according to the invention, the following applies equivalently for the heart period duration analysis:

$$\overline{T_H^2(\mu)} = [\overline{T_H}]^2 + [\overline{\Delta T_H(\mu)}]^2 = [\overline{T_H}]^2 + [S_{TH}]^2.$$

In other words:

The total signal power, which can be determined from the R-R signal, corresponds to the sum of the signal power of the arithmetic signal (the square of the mean heart rate) and the square $s_{TH}^2$ of the standard deviation. This analogously also applies to the information contained in the R-R signal by applying the information theory.

The latter equation for the total signal power can be normalized: division by $\overline{T_H}$ or equivalently multiplication by $[\overline{f_H}]^2$, respectively, so as to obtain according to the invention:

$$\frac{\overline{T_H^2(\mu)}}{[\overline{T_H}]^2} = 1 + \frac{[S_{TH}]^2}{[\overline{T_H}]^2} \text{ and } \overline{T_H^2(\mu)} \cdot [\overline{f_H}]^2 = 1 + [S_{TH}]^2 \cdot [\overline{f_H}]^2$$

From this representation it can be inferred that the normalized R-R total signal power is now variable by the weighted component $$[S_{TH}]^2 \cdot [\overline{f_H}]^2,$$

that is, by weighting the square $s_{TH}^2$ of the standard deviation, the heart rate variability, with the square of the mean heart rate $\overline{f_H}$. This corresponds to the square of the relative heart rate variability (variation coefficient) VHF ($\Delta$HF) and HRV, respectively.

A representation of the cardiovascular state alone by the standard deviation $S_{TH}$ or the absolute heart rate variability, respectively, is not sufficient. With the weighting factor square of the (mean) heart rate—the latter is decisively characterized by the autonomic nervous system with its components sympathetic and parasympathetic nervous systems—the cardiovascular state can, according to the invention, be evaluated in a differentiated manner. This is also demonstrated by the following representations of the FFT analysis of the signal alternating component, the absolute deviation of the heart period duration at the time of the µ-th heartbeat from the arithmetic mean value.

If the introduced absolute deviation of the heart period duration at the time of the µ-th heartbeat from the determined arithmetic mean value $\overline{T_H}$ $$\Delta T_H(\mu) = T_H(\mu) - \overline{T_H}$$

is not subjected to a time averaging, but to a fast Fourier transform (FFT), one obtains the known "(power) spectrum of the heart rate variability", more precisely the "(power) spectrum of the absolute deviations of the heart period duration from the mean value $\overline{T_H}$".

FIG. 6 shows an FFT spectrum derived from a heart period duration tachogram of a 20 year old person in a good cardiovascular condition, wherein the derivation time was 3 minutes. For physical-mathematical reasons the range up to 0.5 Hz is to be used as a basis therefor. As such a frequency analysis is performed merely for the alternating component $\Delta T_H(\mu)$ [of the absolute deviation of the heart period duration from the mean value $\overline{T_H}$] and the same does not include a direct component, the value with f=0 Hz is always zero. However, the total signal $T_H(\mu)$ does include the above-mentioned direct component, the arithmetic mean value $\overline{T_H}$.

So far, there is no uniform standard with respect to the "heart rate variability analysis FFT spectrum", but a great variety of results and theses. With respect to the analyses of spectrums, reference is made more and more often to the guidelines of the Task Force of European Society of Cardiology of 1996 and to the "North American Society of Pacing and Electrophysiology" [Heart rate variability. Standards of measurement, physiological interpretation and clinical use. European Heart Journal (1996) 17, 354-381]. Also the fundamental thesis of Bürklein, M, Vogt L and W Banzer is based on the same: Measuring method for the detection of the heart rate variability—A comparative study. Cross validation of heart rate variability measurements before and after exercise. German magazine for sports medicine, age group 56, No. 12 (2005).

The Task guideline as well as the thesis of Bürklein form the basis for an FFT analysis, which can also be inferred from FIG. 6. Here, the typical frequency ranges for the case of a so-called "short-term analysis" of about 2 to 5 min ECG recording time are characterized in correspondence with the Task guideline. The respective influence of the vegetative components of the cardiovascular system can be inferred therefrom:

Frequency range "Low Frequency" 0.04 to 0.15 Hz: To this range, a mainly sympathetic cardiovascular activity can be assigned, and with it also an occurring psychic and physical stress. In the literature it is stated that also a parasympathetic component can be represented. As is taught by physiology, this range also contains the Traube-Hering oscillations to express the occurring blood pressure periodicities In the literature, a general "strain" or "stress" is assigned to this low frequency range.

Frequency range "High Frequency" 0.15 to 0.4 Hz: Typical for this is the occurring parasympathetic (vagal) activity, therewith respiration-synchronous heart rate fluctuations of the respiratory sinus arrhythmia [Horn, A: Diagnostics of the heart rate variability in sports medicine—frame conditions and methodical bases. Diss, Faculty for sports science, Ruhr-University Bochum 2003].

The spectral area ratio between the LF and HF component is called sympatho-vagal balance. It has to be noted, however, that a change in the LF component—as was mentioned above—can be caused both sympathetically and parasympathetically. This detection and quantification represents a problem not solved so far also with respect to the sympatho-vagal balance.

The low frequency component not marked in FIG. 6 of about 0.01-0.05 Hz represents, inter alia, the thermoregulatory influence. In the literature, the statements in this respect are still very indistinct. As such a frequency analysis and evaluation for the purpose of the known sampling theorem used in signal theory would require substantially longer ECG recording times as compared to the present case relating to telemedical applications, this range has to be excluded. Therefore, an FFT spectrum analysis is carried out only for the characterized frequency range of 0.04 to 0.4 Hz, above all, to quantify also the vegetative influence which is so important for the cardiovascular system. For the purpose of the extended sampling theorem, approximately 5 times to 10 times the time following from the theorem, i.e. about 120 seconds, should be used as minimum analysis duration at a frequency of 0.04 Hz.

Methodical requirements for the performance of an FFT analysis are, inter alia, a steady state and interference freedom of the R-R recording, which are to be ensured in a prepared reprocessing of the R-R series (trend elimination, filtering of artifacts, resampling and others). Due to the demand for a steady state, such a frequency analysis is sensible only for short recording periods of 2 to 5 min—"short-term analysis". This corresponds to the value derived above from the extended sampling theorem, which has proved to be expedient for telemetric applications. A prerequisite for the derivation of normal values is that the ECG is recorded in a resting state and that the measurement is commenced only when the circulation system is in a steady state. With sufficient approximation this is the case after about 2 minutes.

FIGS. 7 and 8 show embodiments of typical clinical functions of FFT power density spectrums of the absolute deviations of the heart period duration from the mean value $\overline{T_H}$, wherein, as is generally known, a power spectrum corresponds to the squared FFT amplitude spectrum.

FIG. 7 shows the comparing functions of the spectral power densities of a 35 year old resting healthy person and of a type I diabetic of the same age, with a somatovisceral polyneuropathy of a moderate degree, with an ECG measuring time of 5 minutes each. Due to the longer recording time it is additionally possible by approximation to evaluate the low frequency range 0.01 . . . 0.04 Hz. While the components in this range only differ slightly, the differences in the two other ranges are very evident. Above all in the purely vagally conditioned HF band the spectral power is extremely decreased, so that following a sympathetic cardiac innervation, the diagnosis of a distinct vagus disorder had to be made.

FIG. 8 shows in another embodiment the spectrum of a 37 year old patient with Guillain-Barré-Strohl polyradiculitis at the peak of the disease. The components in all frequency ranges are extremely decreased, whereby the ordinate scale was adjusted much more sensitively as compared to FIG. 7, so as to allow a representation of the components. A nearly complete cardiac denervation was diagnosed.

As can inferred from the functions of the spectral power densities in FIGS. 7 and 8, the amplitude components can be qualitatively compared in the defined frequency ranges. Beside normal functions, typical non-normal functions are shown. Therefore, according to the invention, a quantification is performed.

Proceeding from normal values to be derived for the spectral power-normal-amplitudes $A(nf_A)$ in the frequency ranges 0.04 . . . 0.4 Hz, which occur at the discrete frequencies $nf_A$ [$f_A$=sampling frequency], pertinent area integrals (sums) F at an ECG recording time for a measurement of 120 seconds in normal subjects are determined as follows (see FIG. 6):

LF – range 0, 04 ... 0, 15 Hz:

$F_{normal\ 0,04\ ...\ 0,15Hz} = \Sigma A(nf_A)$

HF – range 0, 15 ... 0, 4 Hz:

$F_{normal\ 0,15\ ...\ 0,4Hz} = \Sigma A(nf_A)$

According to the invention, the mean normal range for these frequency ranges is determined from these "normal area sums". As is generally known, the following applies in the case of normal distribution: mean value±standard deviation.

If now an optional spectrum is derived, according to the invention, the area sum $F_\lambda$ is formed for the indicated frequency ranges and related to the associated normal area value. These relative values are called "spectral indexes M".

$$M_{LF} = \frac{F_{0,04\ ...\ 0,15\ Hz}}{\text{mean-area-normal-value}} 100[\%]$$

$$M_{HF} = \frac{F_{0,15\ ...\ 0,4\ Hz}}{\text{mean-area-normal-value}} 100[\%]$$

As these spectral indexes are always related to the normal values of the corresponding frequency range, it can be seen immediately whether autonomic dysbalances occur.

In FIG. 9 the embodiments shown are two typical cases for spectral indexes, which can be derived from determined heart period duration tachograms (R-R intervals) of a tele-ECG:
  normal subject: hardly any stress state, good recovery state with distinct respiratory sinus arrhythmia (analogously to FIG. 4a)),
  coronary patient with small recovery component (corresponding to FIG. 4b)).

It follows from the FFT spectrums according to FIGS. 6 to 8 that the evaluation frequency range of 0.04 to 0.4 Hz defined according to the guidelines of the Task Force of European Society of Cardiology and the North American Society of Pacing and Electrophysiology of 1996 dominantly determines the activity of the vegetative component of the cardiovascular system and, according to the invention, shall be analyzed more profoundly below for the purpose of the signal theory, while the frequency range of about 0.01 to 0.04 Hz characterizing the thermoregulatory influence shall be disregarded in the present telemedical application due to the required longer ECG recording times. Moreover, the following considerations are based on a corresponding trend correction.

Consequently, it can be assumed with sufficient approximation that the spectral FFT power density spectrum areas of the defined frequency range of 0.04 to 0.4 Hz correspond to the square of the standard deviation $s_{TH}^*$, wherein, contrary to $s_{TH}$, $s_{TH}^*$ only represents the part of the standard deviation that is determined by the two vegetative components of the autonomic nervous system.

According to the invention it is assumed:

$$\int_{0,04}^{0,4\ Hz} \text{power density spectrum} \approx [S_{TH}^*]^2 = [S_{THvegetative}]^2$$

and $$\int_{0,04}^{0,15\ Hz} \text{power density spectrum} + \int_{0,15}^{0,4\ Hz} \text{power density spectrum} \approx$$

$$[S_{TH\ vegetative}]^2$$

Accordingly, the heart rate variability $s_{TH}{}^*$, which can be assigned to the two components of the autonomic nervous system, the sympathetic and parasympathetic nervous systems, can be determined from the two area components $F_{0.04\ldots0.15\,Hz}$ and $F_{0.15\ldots0.4\,Hz}$.

It was already shown that a quantitative representation of the cardiovascular state for the purpose of the parallel-axes theorem used in signal theory by $s_{TH}{}^2$ alone, and thus also by the power density spectrum, is not sufficient, but that, by introducing the weighting factor "square of the (mean) heart rate", the cardiovascular state can be represented and controlled to a greater extent with respect to the influence of the autonomic nervous system. Thus, it follows:

$$[\overline{f_H}]^2 \int_{0.04}^{0.4\,Hz} \text{power density spectrum} \approx [\overline{f_H}]^2 [S_{TH\,Vegetative}]^2$$

and $$[\overline{f_H}]^2 \int_{0.04}^{0.15\,Hz} \text{power density spectrum} +$$

$$[\overline{f_H}]^2 \int_{0.15}^{0.4\,Hz} \text{power density spectrum} \approx [\overline{f_H}]^2 [S_{TH\,vegetative}]^2.$$

Assuming in short $$\int_{0.04}^{0.15\,Hz} \text{power density spectrum} = F_{0.04\ldots0.15\,Hz} = A$$

$$\int_{0.15}^{0.4\,Hz} \text{power density spectrum} = F_{0.15\ldots0.4\,Hz} = B,$$

one obtains, according to the invention, for the weighted addends $$[\overline{f_H}]^2 A + [\overline{f_H}]^2 B \approx [\overline{f_H}]^2 [S_{THvegetative}]^2.$$

Thus, $$[\overline{f_H}]^2 A \text{ and } [\overline{f_H}]^2 B$$

can be defined as weightings. Is, for example, the addend A already greater than normal, it will be considerably increased by the weighting with the square of $\overline{f_H}$ in the case of a tachycardiac heart rate. Although this likewise relates to the addend B, it may be substantially smaller than A because a respiratory sinus arrhythmia is then hardly present.

Consequently, with this weighting the following activity dimensions of the autonomic nervous system can be defined with respect to the cardiovascular system:

dimension for sympathetic activity, stress, strain $\sim[\overline{f_H}]^2 A$ dimension for parasympathetic activity, relaxation and recovery $\sim[\overline{f_H}]^2 B$ With such an approach, always the entire R-R signal is analyzed with respect to the effect on the cardiovascular system, and not only the alternating component $\Delta T_H(\mu)$. This also refers to the following considerations as regards other weighting variants.

While a sympathetic activity increases the heart rate, it is decreased by a parasympathetic one. According to the invention, this can be realized quantitatively by the following weighting 2:

$$[\overline{f_H}]^2 A \text{ and } \frac{B}{[\overline{f_H}]^2}.$$

Thus, as compared to the parasympathetic one, the sympathetic activity component of the LF component can mathematically be increased even more strongly than in weighting 1. For the activity dimensions of the autonomic nervous system one obtains analogously to weighting 1:

dimension for sympathetic activity, stress, strain $\sim[\overline{f_H}]^2 A$ dimension for parasympathetic activity, relaxation and recovery $\sim$ $$\frac{B}{[\overline{f_H}]^2}$$

As the HF range of the FFT already exclusively characterizes the parasympathetic (vagal) activity of the autonomic nervous system, a weighting of this range for the purpose of physiology is not necessary, so that as third weighting variant the following can be defined:

$$[\overline{f_H}]^2 A \text{ and } B.$$

Consequently, the following applies:

dimension for sympathetic activity, stress, strain $\sim[\overline{f_H}]^2 A$ dimension for parasympathetic activity, relaxation and recovery $\sim B$.

It was stated that in the literature the spectral area ratio between the LF and the HF component is designated as sympatho-vagal balance. For the introduced weightings one obtains:

Weighting 1:

With $$[\overline{f_H}]^2 A + [\overline{f_H}]^2 B \approx [\overline{f_H}]^2 [S_{THvegetative}]^2.$$

according to the invention, the balance is represented as ratio A/B, so that such a weighting does not alter the balance. This is a problem if the spectral frequency components in the LF range are mainly vagally conditioned. The result thereof would be that this would erroneously be represented as disturbed balance.

Weighting 2:

$$\text{sympathiko-vagal balance} = \frac{A}{B}[\overline{f_H}]^4.$$

From this follows that an increased heart rate leads to a considerable disorder of the sympatho-vagal balance (increase with the $4^{th}$ power of $\overline{f_H}$], which also proves to be a correct objective under the physiological aspect. If, consequently, the LF component is increased, and correspondingly the sympatho-vagal balance inventively introduced by a separate addend weighting, only an increased sympathicus activity can be the cause, and not the parasympathicus.

Weighting 3:
Analogously it is assumed:

$$\text{sympathiko-vagal balance} = \frac{A}{B}\overline{[f_H]}^2.$$

With this weighting, too, an increased heart rate leads to an increase of the sympatho-vagal balance, though with the second power of $\overline{f_H}$ corresponding to the general definition of the signal power. Therefore, this weighting forms the basis as preferred variant.

FIG. 10 shows a smoothed FFT spectrum of a 28 year old resting normal person, which is derived from the tachogram of the heart period durations, with the maximums occurring at 0.1 and about 0.25 Hz. As a characteristic exemplary embodiment, the represented derivation of the indexes shall hereinafter be specified more precisely for the purpose of the introduced weightings.

In the FFT spectrum discrete spectral power amplitudes $A(nf_A)$ are represented, wherein the interval of the spectral amplitudes is defined by the sampling frequency $f_A$. The envelope of $A(nf_A)$ and the sum of areas for the respectively defined frequency range is a dimension for the vegetative cardiovascular state.

First Step: Derivation of Normal Values

The R-R tachograms derived from normal persons, with an ECG recording time for a measurement of 120 seconds and a sampling frequency of about 1000 Hz, are subjected to an FFT analysis so as to represent the amplitudes $A(nf_A)$. As the derivation time is constant, and as it can also be assumed that the number of the R-R intervals forming the basis of a measurement are subject to a "normal" spread, all amplitudes $A(nf_A)$ of the N normal persons are "superimposed", and the associated mean value and the standard deviation are determined for each frequency $nf_A$. From this follows a graphical representation of these mean values as spectrum, including spread at each spectral line. Subsequently, a curve smoothing has to be performed. The so obtained values are to be stored as normal values $A(nf_A)_{normal}$ in the computer.

In a generalizing manner it can be derived from FIG. 10:
In the normal case, 1 maximum occurs in each range:
in the LF range at about 0.1 Hz
in the HF range at about 0.25 Hz
These respective amplitude maximums at the frequencies of 0.1 and 0.25 Hz are set as standard values of both ranges LF, HF:

$$A_{LF\,max} \text{ and } A_{HF\,max}.$$

Each spectral amplitude in the respective frequency range is divided by the pertinent amplitude maximum $A_{LF\,max}$ and $A_{HF\,max}$, so that a normalized representation is obtained. Thus, one obtains the amount One as respective maximum value for both the LF and the HF range. The standard deviation is normalized correspondingly.

If an optional spectrum has the spectral amplitudes $A(nf_A)_{optional}$, these values are to be normalized as well, i.e. they are to be divided by the amplitude maximums (standard values) $A_{LF\,max}$ and $A_{HF\,max}$. Thus, one obtains a normalized and dimensionless spectrum, in which the deviations from the normal function are qualitatively discernable immediately, in both frequency ranges. If the spectral area in the range of 0.04 . . . 0.15 Hz exceeds that of the normal function, an abnormal case occurs, analogously to an area reduction of 0.15 . . . 0.4 Hz as compared to the normal case.

Second Step: Derivation of Area Indexes

The optional and normalized power spectrum derived in a first step thus shows possible qualitative differences over the normal case. In a second step, the quantitative indexes for this are to be determined.

From the normalized spectral functions derived in step 1 for the respective frequency ranges 0.04 . . . 0.15 and 0.15 . . . 0.4 Hz the area integrals can be determined if 0.04 . . . 0.15 Hz and 0.15 . . . 0.4 Hz are set as integration limits.

Algorithms:
Normal Case:
Determination of both area integrals of the averaged "normal spectrum":

$$F_{normal\,0,04\ldots0,15\,Hz} = \sum_{0,04\ldots0,15\,Hz} \frac{\text{spectral amplitude } A(nf_A)}{A_{LF\,max}},$$

$$F_{normal\,0,15\ldots0,4\,Hz} = \sum_{0,15\ldots0,4\,Hz} \frac{\text{spectral amplitude } A(nf_A)}{A_{HF\,max}}.$$

Optional Case:
As to the optional case, it applies analogously:

$$F_{0,04\ldots0,15\,Hz} = \sum_{0,04\ldots0,15\,Hz} \frac{\text{spectral amplitude } A(nf_A)}{A_{LFmax}} \text{ and}$$

$$F_{0,15\ldots0,4\,Hz} = \sum_{0,15\ldots0,4\,Hz} \frac{\text{spectral amplitude } A(nf_A)}{A_{HFmax}},$$

Indexes Derived from the Area Integrals

According to the invention, these area integrals can be normalized by the division by the respective mean area-normal-value, so that one obtains "spectral indexes M" as quantitative dimensionless quantities:

$$M_{LF} = \frac{F_{0,04\ldots0,15\,Hz}}{F_{normal\,0,15\ldots0,4\,Hz}} 100[\%]$$

$$M_{HF} = \frac{F_{0,15\ldots0,4\,Hz}}{F_{normal\,0,04\ldots0,15\,Hz}} 100[\%]$$

Third Step: Specifying the Derived Spectral Indexes More Precisely

According to the invention it was explained how specifically the LF frequency range of the FFT spectrum can be weighted, so as to detect a sympathetic activity component occurring therein as compared to the parasympathetic one. In relation to the pertinent area integrals $F_{0,04\ldots0,15\,Hz}$ and $F_{0,15\ldots0,4\,Hz}$, and thus also to the absolute measures $M_{LF}$ and $M_{HF}$, these are to be weighted with the square of the mean heart rate.

It is known from physiology that 60 . . . 80 $\text{min}^{-1}$ are assumed to be the normal range (normal sinus rhythm) of the mean heart rate, whereby a mean normal value of 72 $\text{min}^{-1}$ is specified by Schmidt and Thews [Schmidt, R F and G Thews: Physiology of the human being. 27. Edition. Springer Berlin Heidelberg New York 1997]. As normalizing value for the weightings to be carried out, the "mean" of the introduced physiological normal range of 70 $\text{min}^{-1}$ is assumed with sufficient approximation.

Thus, the derived spectral indexes can be specified more precisely by corresponding weightings with the normalized heart rate, wherein the heart rate is set in [min$^{-1}$] and relative figures are assumed for the indexes:

1. Weighting:

$$M_{LF} \cdot \left[\frac{\overline{f_H}}{70 \text{ min}^{-1}}\right]^2 = M_{LF}^+,$$

$$M_{HF} \cdot \left[\frac{\overline{f_H}}{70 \text{ min}^{-1}}\right]^2 = M_{HF}^+$$

$$\text{sympatho-vagal balance } 1 = \frac{M_{LF}^+}{M_{HF}^+} = \frac{M_{LF}}{M_{HF}}$$

Such a weighting does not alter the balance.

2. Weighting:

$$M_{LF} \cdot \left[\frac{\overline{f_H}}{70 \text{ min}^{-1}}\right]^2 = M_{LF}^+$$

(with respect to first case, weighting unchanged)

$$M_{HF} \cdot \left[\frac{70 \text{ min}^{-1}}{\overline{f_H}}\right]^2 = M_{HF}^{++}$$

$$\text{sympatho-vagal balance } 2 = \frac{M_{LF}^*}{M_{HF}^*}$$

By inserting the corresponding indexes, it follows $$\text{sympatho-vagal balance } 2 = \frac{M_{LF}}{M_{HF}} \cdot \left[\frac{\overline{f_H}}{70 \text{ min}^{-1}}\right]^4 \text{ and}$$

$$\text{sympatho-vagal balance } 2 = [\text{sympatho-vagal balance } 1] \cdot \left[\frac{\overline{f_H}}{70 \text{ min}^{-1}}\right]^4$$

Thus, one obtains as ratio of the weighted balances 2 and 1

$$\frac{\text{sympatho-vagal balance } 2}{\text{sympatho-vagal balance } 1} = \left[\frac{\overline{f_H}}{70 \text{ min}^{-1}}\right]^4.$$

3. Weighting:

$$M_{LF} \cdot \left[\frac{\overline{f_H}}{70 \text{ min}^{-1}}\right]^2 = M_{LF}^+$$

(with respect to first case, weighting unchanged)

$$M_{HF_{\text{sympatho-vagal balance } 3}} = \frac{M_{LF}^*}{M_{HF}^*}$$

$$= \frac{M_{LF}}{M_{HF}} \cdot \left[\frac{\overline{f_H}}{70 \text{ min}^{-1}}\right]^2$$

As ratio of the weighted balances 3 and 1 it follows immediately $$\frac{\text{sympatho-vagal balance } 3}{\text{sympatho-vagal balance } 1} = \left[\frac{\overline{f_H}}{70 \text{ min}^{-1}}\right]^2.$$

FIG. 11 represents the ratio $V_{balances}$ of the defined balances in dependence on the heart rate. It can be seen that higher rates strongly increase this ratio, while rates lower than the normal value of $f_H$=70 min$^{-1}$ clearly reduce this ratio. This entirely corresponds to the physiological behavior, as higher heart rates increase the sympathicus and thus the stress component, while the rates below the normal value activate the parasympathicus, thereby reducing the stress. Examples are (s. FIG. 11):

$\overline{f_H}$=50 min$^{-1}$: A weighting 2 reduces with respect to weighting 1 the ratio $V_{2;1}$ to 0.26, the weighting 3 to $V_{3;1}$=0.51.

$\overline{f_H}$=90 min$^{-1}$: Here, the ratios are increased to $V_{2;1}$=2.73 and $V_{3;1}$=1.65.

FIG. 12a to e) show as further embodiments electrocardiograms of a 30 year old lying test person (smoker), each obtained in a rest position with a recording time of 2 minutes, subject to reflex vasoconstriction, hyperventilation (deeper breast breathing) with 6 and 10 min$^{-1}$, respectively.

While in the rest position shown in FIG. 12a) the indexes for both stress and relaxation are considerably lower than the normal values, while the sympatho-vagal balance 3=1.04 is exactly in the normal range, the ratios in FIG. 12b) vary strongly. By a sudden passive immersion of the hand into ice water, a sympathetic excitation wave is initiated, which reduces the cardiovascular microcirculation, increases the heart rate. It clearly shows that the stress index is increased by a factor of 4 at the typical frequency maximum of 0.1 Hz, while the relaxation index remains unchanged. By this, the balance 3 is increased to 4.84 as an expression of the initiated sympathetic excitation wave. This change is a completely normal cardiovascular behavior, a cardiovascular autonomic neuropathy can be excluded.

In FIGS. 12 c) and d) the ratios of the same person in a lying state were derived under the physiological function tests deeper breast breathing (hyperventilation) with 6 and 10 min$^{-1}$. As was expected, the different frequencies result in completely changed balances 3. While with 6 min$^{-1}$≡0.1 Hz a clear maximum in the LF range of the FFT spectrum is represented, the heart microcirculation is correspondingly reduced, the stress index $M_{LF}$* is increased to 5.9 and likewise the balance with a minimum relaxation index to 15, the ratios under the deeper breathing of 10 min$^{-1}$≡0.167 Hz, i.e. within the HF range of the FFT spectrum, change to the contrary: due to the increased relaxation index of 4.4, at a minimum sympathicus activity, the balance goes to the minimum value 0.1.

FIG. 12 e) shows sections of the tele-ECGs derived with 6 and 10 min$^{-1}$. Clearly recognizable are the different R-R intervals both during inspiration and expiration, however, also in the cardiovascular characteristics as a whole. Thus, the deep breast breathing of 6 min$^{-1}$≡0.1 Hz, as compared to 10 min$^{-1}$≡0.167 Hz, effects as a result of the sympathicus activation a higher heart rate, shorter heart period durations and a greater relative heart rate variability.

The heart period duration changes in FIG. 13 were surprisingly derived from corresponding tele-ECGs of a myocardial infarction patient during ergometer exercise, which, however, also basically showed in tests with professional cyclists when exposed to considerable stress. In these cases, no respiratory dependency of the heart periods can be seen in the heart period duration tachograms, but these behave nearly like an electronic multivibrator: periodic oscillations with a period doubling tendency occur. Obviously these conditions of the non-linear cardiovascular system are adopted during the change from order to chaos, which was discovered for the first time by the physicist Feigenbaum in 1976, when he examined different equations with period doubling behaviors. In general, Feigenbaum discovered that, when the order collapses and changes over to chaos, a period doubling represents, for the purpose of the chaos theory, a typical manifestation in non-linear systems, which was also found, for example, in chemical Belusow-Zhabotinsky reactions. As is shown by the periodic changes of the heartbeats in FIG. 13, these relations can obviously also be applied to the cardiovascular system, so that, after a heart period duration doubling has occurred, a complete myocardial chaos can start as critical condition.

If an R-R behavior corresponding to FIG. 13 (right) is now subjected to an FFT transformation, abnormally higher components appear in the extended HF spectrum range, so that this range of about 0.35 . . . 0.5 Hz represents the present cardiovascular risk more precisely, but not yet sufficiently. The occurring limits cannot be represented, because an FFT spectrum can only be represented up to 0.5 Hz. According to the invention it showed that a frequency analysis of the derived ECG total time function of 0 to about 2 Hz leads to a problem solution, which follows from FIG. 14. If an exact heart rate doubling occurs at a same amplitude, the possible critical cardiovascular condition with a changeover to the myocardial chaos has occurred. While at the time "no stress" the dominant frequency is f=1,234 Hz 74 min$^{-1}$ and corresponds to the mean heart rate, the spectral components clearly change under stress of about 50 W: f=0.813 Hz a 49 min$^{-1}$ represents the mean rate of the one mean heart periodicity, though with nearly the same spectral amplitude as the one of the other mean heart rate f=91 min$^{-1}$. Under this stress, the critical condition is obviously not yet reached. If the stress is then set again to zero, the normal conditions are readopted.

According to the invention, a (stability) criterion $K_\mu$ for the (non-linear) cardiovascular system is to be derived from the frequency spectrums, so as to preclude a starting myocardial chaos, if possible.

If one sets, instead of heart rate $f_H$, the pertinent heart period duration $T_H$ $$f_H [Hz]=1/T_H [s],$$

the following applies to an amplitude spectrum according to FIG. 14

$$f_{H1}=1/T_{H1}, f_{H2}=1/T_{H2}.$$

If, in the borderline case, a doubling of the heart periodicity according to FIG. 13 occurs, this applies to the rate $f_{H2}$, i.e. to $T_{H2}$, due to the reciprocal interrelation. Consequently, the following must apply to the stability with respect to the rate:

$$T_{H2} \leq 2T_{H1}$$

and $$f_{H2} \geq \frac{1}{2} f_{H1}.$$

respectively. Therefore, in the borderline case of the doubling of the heart period duration, the following is valid with respect to the rate:

$$f_{H2} = \frac{1}{2} f_{H1},$$

while the pertinent amplitudes $A_{f1}$ and $A_{f2}$ here have to show the same amount. According to the invention, the following is to be formulated therefrom by approximation as (stability) criterion $K_\mu$ for the cardiovascular system, derived from the ECG time function:

$$K_{frenquency} = \frac{f_1}{f_2} < 2$$

$$K_{amplitude} = \frac{A_{f2}}{A_{f1}} < 1$$

The representation of the cardiovascular condition by a telemedical data transfer to the display of a mobile radio device or, generally, to a peripheral terminal as a component of the telemedical overall system "cardiac complex analyzer" is shown in FIG. 15.

According to the invention, the mean heart rate, the heart rate variability, indexes for stress and relaxation as well as the weighted sympatho-vagal balance are represented on two surfaces designed in a tachometer-like manner, wherein the measured values can be compared with normal values and ranges derived in a lying rest position. In a surface modification the pointer is stationary, while the scale components are marked variably in response to their values. In case of the normal value detection it showed that in connection with the components stress, relaxation and balance, a logarithmic normal distribution can be assumed, thereby also allowing, in accordance with the invention a corresponding design of these scale divisions.

FIG. 16 shows an embodiment according to the invention. Analogously to the known automobile and aircraft black box, in which corresponding technical parameters are temporarily stored for the purpose of a subsequent evaluation, there not only is the possibility of the direct telemedical transmission and evaluation in a receive station and a possible feedback by the doctor, but also a detection of vital data takes place, especially ECG, blood pressure and blood oxygen saturation, in a special medical data and monitoring box in the passenger car, truck or aircraft. After the detection, the data can be transferred directly or by means of a Bluetooth function to the box for the purpose of their subsequent evaluation. It can be seen that a permanent vehicle localization is possible via satellite and, thus, in an emergency also a communication between corresponding persons in the vehicle and the receive station, specifically also the doctor.

FIG. 17 shows the total communication process from the ECG recording and storage, and of the telemedical data transfer by using the most various analog and digital communication paths, such as telephone, internet, intranet, radio, infrared, Bluetooth, to central or decentralized servers/databases. Moreover, the communication cycle comprises the forwarding and visualization to end users, such as hospitals, doctors, other users, and the feedback and reaction after the diagnosing. The invention comprises the retrieval of the stored data by a PC from the data logger (ECG sensor).

To realize the introduced method, a device is necessary. FIG. 18 shows the known general schematic representation of a telemedical ECG sensor, including signal processing and storage, as well as user interface and transmit unit.

An essential requirement for the use of such systems is basically a simplification of the operation, as the sensor shall also be applied by physically restricted patients themselves, without the assistance of additional medical staff.

According to the invention, FIG. 19 shows the realization of a 1-key principle for the telemedical sensor system as defined above in such a way that only one single key is connected to the power logic and, at the same time, to a microcontroller. The power logic includes a self-holding function and, as of the first keystroke, provides the device with a voltage until a switching off takes place. The initial state "OFF" is exited at the first keystroke. At the same time, the voltage supply of the measuring system is activated. The reached state "readiness1" activates an electrode impedance measurement to be described later, or a capacitance measurement, which starts the recording when there is a good skin contact with a pair of electrodes. If within a time window no skin contact was detected, a change to the state "OFF" takes place. If within this time window the key is pressed repeatedly, the transmission of the data is initiated. The state "readiness2" reached after the transmission allows an immediate repetition of the transmission and informs the user acoustically/visually about an accomplished transmission. If no more keys are pressed, a timer expires and switches the system off. Depending on the given electrode configuration (open/closed), the introduced invention permits the start or abortion of the recording.

As was explained, an essential problem in telemedicine resides in the reduction of the amount of data to the necessary minimum. Moreover, it can be assumed that, on principle, complete coverage mobile radio networks are available worldwide. However, the characteristic of the asymmetric transmission capacities in the transmit and receive direction limits a mobile data collection, as they are optimized in respect of the reception of data, while only small data transmission rates are available in the transmit direction.

According to the invention, the present telemedical problem definition requires that the R-R intervals are already detected from the high-resolution signal on the ECG sensor. Thus, it is possible to achieve the resolution of about 1 millisecond required for the method, without having to transmit substantially more redundant data. At the same time, it is achieved that artifacts occurring in common methods with high compression factors become meaningless. According to the invention it is, therefore, possible to transmit merely a signal-averaged ECG, consisting of a mean value and a standard deviation.

The telemedical problem definition requires the use of at least 2 electrode systems:
  fixed electrodes on the device (no incidentals required, advantageous for use in spas),
  adhesive electrodes (long recording times and standard deviations possible during exercise and motion, medical use).

For the purpose of the easier and more reliable telemedical application of fixed electrodes it is indispensable to monitor the contact pressure and, thus, the contact resistance electrode/skin during the measurement and, if necessary, to signalize the reduction of the contact pressure.

Known methods used for this purpose are the evaluation of the DC offsets during feeding a DC voltage by means of a comparator, or the evaluation of a superposed AC voltage with a frequency higher by multiples than the wanted signal (>20 kHz), which can also be supplied by an additional electrode on the body. The first method is simple, but often not reliable enough. The second one requires a higher circuit complexity.

According to the invention, the electrode detection in the device is realized as follows: Contrary to prior solutions, wherein a test signal is evaluated and processed on the input side upstream of the instrument amplifier, the analysis of the test signal is performed after the amplification and A/D conversion by means of specific algorithms used in digital signal processing. A test signal having a higher frequency and constant amplitude is added to the actual measured signal, which is attenuated by the patient who is connected in parallel to the input voltage divider. The amplitude of the higher-frequency test signal is, therefore, proportional to the impedance of the electrode-skin transition. The block diagram for the amplitude detection is shown in FIG. 20.

After the A/D conversion, the amplitude is calculated by specific algorithms used in digital signal processing. To this end, it is required to multiply the output signal of the instrument amplifier by sine and cosine. The frequency of the test signal is assigned as parameter to the two harmonic functions. To easily determine the value of the function a sine table is used. The number of the elements of this table results from the ratio of the sampling frequency of the A/D converter to the frequency of the harmonic oscillation. The result of both multiplications is filtered by a low-pass filter. The searched for amplitude is the square root of the sum of the squares of these two filtered signals.

With a ratio of sampling to test frequency of four, the sine table required for the evaluation of the amplitude of the test signal is simplified to the values [0, 1, 0, −1]. This simplification requires a synchronous clock pulse of the A/D converter and D/A converter. Based on this ratio, a test signal frequency of 500 Hz is obtained from a sampling frequency of 2 kHz.

With a fed frequency of 500 Hz and an upper limit frequency of 1 kHz and with a high amplification of the difference amplifier, the amplitude of the fed 500 Hz is too dominant. This behavior requires a defined upper limit frequency of the difference amplifier, which is lower than 500 Hz and does not attenuate the wanted signal.

A limit frequency of the instrument amplifier was set, according to the invention, by optimization to 116 Hz, so as to prevent too high a measurement amplitude superimposed on the wanted signal and, thus, the operation within the limitations. The operation within the limitations is not permissible because, in this case, no detection of the amplitude of the 500 Hz signal results in the value of ~0, thereby signaling a low contact resistance.

The result of this optimization is a test signal amplified by the instrument amplifier and subsequently attenuated by a low-pass filter. With open electrodes this test signal behaves according to FIG. 21. The reduction of the amplitude of the test signal as a result of a low contact resistance to about 20% can be seen in FIG. 22.

What is claimed is:

1. Method for deriving and evaluating cardiovascular information from electrocardiograms to determine sympatho-vagal balance, especially for telemedical applications, comprising:
  using a signal processor for the reduction of data, a mean value and a standard deviation are initially determined as signal-averaged ECG from the high-resolution signal of a recorded ECG over the total recording time and the R-R intervals are subsequently evaluated by means of a detection algorithm, and only the received results are transmitted and/or recorded for the purpose of the data reduction for which purpose from an FFT spectrum of the determined heart period durations area integrals F are determined for the defined LF and HF frequency ranges of 0.04 to 0.15 Hz and 0.15 to 0.4 Hz and are related to the mean area-normal-values, so that spectral indexes for the evaluation are obtained as follows:

$$M_{LF} = \frac{F_{0,04...0,15\ Hz}}{\text{mean-area-normal-value}} 100[\%]$$

$$M_{HF} = \frac{F_{0,15...0,4\ Hz}}{\text{mean-area-normal-value}} 100[\%]$$

wherein further a weighting of the square $s_{TH}^2$ of the standard deviation, the absolute heart rate variability, with the square of the mean heart rate $\overline{f_H}$ is performed $$[s_{TH}]^2 \cdot [\overline{f_H}]^2,$$

so that the cardiovascular state can be evaluated with respect to the influence of the autonomic nervous system with its components sympathicus and parasympathicus, and determining by weightings of the indexes MLF and MHF with the square of the mean heart rate $\overline{f_H}$ how the sympatho-vagal balance B varies, so that the sympathetic activity components occurring in the LF frequency range become quantifiable as compared to the parasympathetic activity components.

2. Method according to claim 1, characterized in that a quantification is performed ;with the weighted indexes as follows;

normalized dimension for sympathetic activity, stress arid strain:

$$M_{LF} \cdot \left[\frac{\overline{f_H}}{70\ \text{min}^{-1}}\right]^2 = M_{LF}^+,$$

normalized dimension for parasympathetic activity, relaxation and recovery:
$M_{Hf}$
sympatho-vagal balance:

$$\text{sympatho-vagal balance} = \frac{M_{LF}^*}{M_{HF}}$$
$$= \frac{M_{LF}}{M_{HF}} \cdot \left[\frac{\overline{f_H}}{70\ \text{min}^{-1}}\right]^2.$$

3. Method according to claim 1, characterized in that beside the R-R. determination it is determined by a frequency analysis of the derived ECG total time function in the range of 0 to about 2 Hz whether two dominant frequency lines $f_{1,2}$ in the from of a frequency doubling occur at a same amplitude $A_{f1,2}$, so as to define a (stability) criterion $K_\mu$ for the actually non-linear cardiovascular system, derived from the ECG time function, as follows:

$$K_{frequency} = \frac{f_1}{f_2} < 2$$

$$K_{amplitude} = \frac{A_{f2}}{A_{f1}} < 1.$$

\* \* \* \* \*